(12) United States Patent
Jackson et al.

(10) Patent No.: US 11,045,652 B2
(45) Date of Patent: Jun. 29, 2021

(54) DETERMINATION OF THERAPY ELECTRODE LOCATIONS RELATIVE TO OSCILLATORY SOURCES WITHIN PATIENT

(71) Applicant: Medtronic, Inc., Minneapolis, MN (US)

(72) Inventors: Jadin C. Jackson, Roseville, MN (US); Yizi Xiao, Eden Prairie, MN (US); Paula Andrea Elma Dassbach Green, Minneapolis, MN (US); Jianping Wu, Chapel Hill, NC (US); Christopher L. Pulliam, Plymouth, MN (US); Eric J. Panken, Edina, MN (US); Robert S. Raike, Minneapolis, MN (US); Scott R. Stanslaski, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 82 days.

(21) Appl. No.: 16/395,320

(22) Filed: Apr. 26, 2019

(65) Prior Publication Data
US 2020/0338353 A1    Oct. 29, 2020

(51) Int. Cl.
*A61N 1/36*    (2006.01)
*A61N 1/05*    (2006.01)
*A61N 1/372*    (2006.01)

(52) U.S. Cl.
CPC ...... *A61N 1/36185* (2013.01); *A61N 1/0534* (2013.01); *A61N 1/36007* (2013.01);
(Continued)

(58) Field of Classification Search
None
See application file for complete search history.

(56) References Cited

U.S. PATENT DOCUMENTS

| 4,445,512 A | 5/1984 | Krupka et al. |
| 6,711,547 B1 | 3/2004 | Glover et al. |

(Continued)

FOREIGN PATENT DOCUMENTS

| WO | 2016/030424 A1 | 3/2016 |
| WO | 2018080653 A1 | 5/2018 |

OTHER PUBLICATIONS

De Solages et al., "Maximal Subthalamic Beta Hypersynchrony of the Local Field Potential in Parkinson's Disease is Located in the Central Region of the Nucleus," Journal of Neurology, Neurosurgery, and Psychiatry, vol. 82, Jan. 4, 2011, pp. 1387-1389.
(Continued)

*Primary Examiner* — Brian T Gedeon
(74) *Attorney, Agent, or Firm* — Shumaker & Sieffert, P.A.

(57) ABSTRACT

Techniques are described determining electrodes that are proximate or distal to location of an oscillatory signal source in a patient based on current source densities (CSDs). Processing circuitry may determine, for one or more electrodes of a plurality of electrodes, respective time-varying measurements of CSDs, aggregate, for the one or more electrodes of the plurality electrodes, the respective time-varying measurements of the CSDs to generate respective average level values for the one or more electrodes of the plurality of electrodes, determine, for one or more electrodes of the plurality of electrodes, respective phase-magnitude representations of the time-varying measurements of the CSDs. The respective phase-magnitude representations are indicative of respective magnitudes and phases of a particular frequency component of respective time-varying measurements of the CSDs. The particular frequency component is a frequency component having a largest transform coef-
(Continued)

ficient in a time-varying measurement of a CSD having a largest average level value.

23 Claims, 13 Drawing Sheets

(52) U.S. Cl.
CPC ...... *A61N 1/36067* (2013.01); *A61N 1/36062* (2017.08); *A61N 1/36071* (2013.01); *A61N 1/37247* (2013.01)

(56) References Cited

U.S. PATENT DOCUMENTS

| | | | |
|---|---|---|---|
| 7,231,258 | B2 | 6/2007 | Moore et al. |
| 7,548,787 | B2 | 6/2009 | Feher et al. |
| 8,280,514 | B2 | 10/2012 | Lozano et al. |
| 8,615,299 | B2 | 12/2013 | Goetz |
| 8,639,335 | B2 | 1/2014 | Peichel et al. |
| 8,700,150 | B2 | 4/2014 | Libbus et al. |
| 9,119,543 | B2 | 9/2015 | Martens |
| 9,572,737 | B2 | 2/2017 | McNeely et al. |
| 9,619,621 | B2 | 4/2017 | Dicks et al. |
| 9,666,061 | B2 | 5/2017 | Reeder et al. |
| 9,813,270 | B2 | 11/2017 | Feher |
| 10,095,837 | B2 | 10/2018 | Corey et al. |
| 10,529,450 | B2 | 1/2020 | Corey et al. |
| 2002/0128563 | A1 | 9/2002 | Carlson et al. |
| 2003/0236487 | A1 | 12/2003 | Knowlton |
| 2004/0073098 | A1 | 5/2004 | Geva et al. |
| 2005/0075067 | A1 | 4/2005 | Lawson et al. |
| 2006/0025824 | A1 | 2/2006 | Freeman et al. |
| 2006/0224191 | A1 | 10/2006 | Dilorenzo |
| 2007/0123758 | A1 | 5/2007 | Miesel et al. |
| 2007/0265669 | A1 | 11/2007 | Roline et al. |
| 2007/0266778 | A1 | 11/2007 | Corey et al. |
| 2008/0083414 | A1 | 4/2008 | Messerges |
| 2009/0099627 | A1 | 4/2009 | Molnar et al. |
| 2009/0264956 | A1 | 10/2009 | Rise et al. |
| 2009/0264967 | A1 | 10/2009 | Giftakis et al. |
| 2010/0029284 | A1 | 2/2010 | Feher |
| 2010/0036269 | A1 | 2/2010 | Ferren et al. |
| 2010/0076514 | A1 | 3/2010 | Cho et al. |
| 2010/0100153 | A1 | 4/2010 | Carlson et al. |
| 2010/0249627 | A1 | 9/2010 | Zhang et al. |
| 2011/0190850 | A1 | 8/2011 | Reinke et al. |
| 2011/0264165 | A1 | 10/2011 | Molnar et al. |
| 2012/0150256 | A1 | 6/2012 | Martens |
| 2012/0154582 | A1 | 6/2012 | Johnson et al. |
| 2013/0172774 | A1 | 7/2013 | Crowder et al. |
| 2013/0218232 | A1 | 8/2013 | Giftakis et al. |
| 2014/0074187 | A1* | 3/2014 | Molnar .............. A61N 1/37211 607/62 |
| 2014/0319921 | A1 | 10/2014 | Lisi et al. |
| 2014/0359508 | A1 | 12/2014 | Otero Diaz et al. |
| 2016/0296759 | A1 | 10/2016 | Cong et al. |
| 2016/0342752 | A1 | 11/2016 | Stueckemann et al. |
| 2017/0079585 | A1 | 3/2017 | Ney et al. |
| 2017/0188993 | A1 | 7/2017 | Hamilton et al. |
| 2017/0259064 | A1 | 9/2017 | Wu et al. |
| 2020/0185093 | A1 | 6/2020 | Corey et al. |

OTHER PUBLICATIONS

Gunalan et al., "Creating and Parameterizing Patient-Specific Deep Brain Stimulation Pathway-Activation Models Using the Hyperdirect Pathway as an Example," PLoS ONE, vol. 12, No. 4, Apr. 25, 2017, 19 pp.
Horn et al., "Toward an Electrophysiological "Sweet Spot" for Deep Brain Stimulation in the Subthalamic Nucleus," Human Brain Mapping, Mar. 2017, 14 pp.
Zaidel et al., "Subthalamic Span of β Oscillations Predicts Deep Brain Stimulation Efficacy for Patients with Parkinson's Disease," Brain, vol. 133, Jun. 9, 2010, pp. 2007-2021.
Tinkhauser et al., "Directional Local Field Potentials: A Tool to Optimize Deep Brain Stimulation," Movement Disorders, Nov. 2017, 6 pp.
U.S. Appl. No. 16/172,435, filed Oct. 26, 2018, by Xiao et al.
International Search Report and Written Opinion of International Application No. PCT/US2020/029129, dated Jul. 2, 2020, 13 pp.
Anderson et al., "Phase-dependent stimulation efects on bursting activity in a neural network cortical simulation," National Institutes of Health, Epilepsy Research, vol. 84, No. 1, Mar. 2009, 23 pp.
Bi et al., "Synaptic Modifications in Cultured Hippocampal Neurons: Dependence on Spike Timing, Synaptic Strength, and Postsynaptic Cell Type," The Journal of Neuroscience, vol. 18, No. 24, Dec. 15, 1998, 9 pp.
Bliss et al., "Long-Lasting potentiation of Synaptic Transmission in the Dentate Area of the Anaesthetized Rabbit Following Stimulation of the Perforant Path," National Institute for Medical Research, Journal of Physiology, vol. 232, Feb. 12, 1973, 26 pp.
Canolty et al., "High Gamma Power Is Phase-Locked to Theta Oscillations in Human Neocortex," Science Magazine, Science, vol. 313, Sep. 15, 2006, 4 pp.
Canolty et al., "The functional role of cross-frequency coupling," Trends in Cognitive Sciences, vol. 14, No. 11, Nov. 2010, 10 pp.
Chang et al., "Normal EEG and Sleep: Adults and Elderly," Chapter 11 Part II, Normal EEG, Electroencephalography: Basic Principals, clinical applications and related fields., Lippincott, Williams and Wilkins, Sixth Edition, 2005, 32 pp.
Chen et al., "Real-Time Brain Oscillation Detection and Phase-Locked Stimulation Using Autoregressive Spectral Estimation and Time-Series Forward Prediction," Biomedical Engineering, vol. 60 Issue 3, IEEE, Published Jan. 31, 2011, Date of current version Mar. 11, 2013, 10 pp.
Chen et al., "Real-Time Brain Oscillation Detection and Phase-Locked Stimulation Using Autoregressive Spectral Estimation and Time-Series Forward Prediction," National Institutes of Health, IEEE Transactions on Biomedical Engineering, vol. 60, No. 3, Mar. 2013, 25 pp.
Cole, "Rectification and Inductance in the Squid Giant Axon," College of Physicians and Surgeons, Retrieved from pg.rupress.org, The Journal of General Physiology, Sep. 20, 1941, 23 pp.
Colgin et al., "Gamma Oscillations in the Hippocampus," International Union of Physiological Sciences/American Physiological Society, Physiology, vol. 25, Oct. 2010, 11 pp.
Da Silva, EEG Analysis: Theory and Practice, Chapter 54 Part IX, Computer-Assisted EEG Analysis, Electroencephalography: Basic Principals, clinical applications and related fields., Lippincott, Williams and Wilkins, Sixth Edition, 2005, 31 pp.
Da Silva, "Neurocognitive Processes and the EEG/MEG," Chapter 50 Part VII, Evoked Potentials and Event-Related EEG Phenomena,Electroencephalography: Basic Principals, clinical applications and related fields., Lippincott, Williams and Wilkins, Sixth Edition, 2005, 30 pp.
Daitch et al., "Frequency-specific machanism links human brain networks for spatial attention," Proceedings of the National Academy of Sciences (PNAS), vol. 110, No. 48, Nov. 26, 2013, 6 pp.
Fell et al., "Phase-locking within Human Mediotemporal lobe predicts memory formation," NeuroImage, vol. 43, No. 2, Elsevier, Jul. 22, 2008, 10 pp.
Fell et al., "The role of phase synchronization in memory processes," Nature Review, Neuroscience, vol. 12, No. 2, Macmillan Publishers Limited, Feb. 2011, 15 pp.
Hanslmayr et al., "Prestimulus Oscillatory Phase at 7 Hz Gates Cortical Information Flow and Visual Perception," Current Biology vol. 23, No. 22, Nov. 18, 2013, 6 pp.
Holscher et al., "Stimulation on the Positive Phase of Hippocampal Theta Rhythm Induces Long-Term Potentiation that Can Be Depotentiated by Stimulation on the Negative Phase in Area CA1 In Vivo," The Journal of Neuroscience, vol. 17, No. 16, Aug. 15, 1997, 8 pp.
Hutcheon et al., "Resonance, Oscillation and the Intrinsic Frequency Preferences of Neurons," Trends in Neuroscience (TINS), vol. 23, No. 5, available online May 3, 2000, 7 pp.

(56) References Cited

OTHER PUBLICATIONS

Hyman et al., "Stimulation in Hippocampal Region CA1 in Behaving Rats Yields Long-Term Potentiation when delivered to the Peak of Theta and Long-Term Depression when Delivered to the Trough," The Journal of Neuroscience, vol. 23, No. 37, Dec. 17, 2003, 7 pp.
Jackson et al., "Computationally efficient, configurable, causal, real-time phase detection applied to local filed potential oscillations," Neuromodulation Divsion, Medtronic Inc, Conference of Neural Engineering, 7 International EEE/EMBS, Apr. 22-24, 2015, 6 pp.
Jacobs et al., "Brain Oscillations Control Timing of single-Neuron Activity in Humans," The Journal of Neuroscience, vol. 27, No. 14, Apr. 4, 2007, 6 pp.
Lebedev et al., "Brain-machine interfaces: past, present and future," Trends in Neurosciences, vol. 29, No. 9, Science Direct, Jul. 21, 2006, 11 pp.
Lega et al., "Human Hippocampal Theta Oscillations and the Formation of Episodic Memories," Hippocampus, vol. 22, No. 4, Apr. 27, 2011, 14 pp.
Pavlides et al., "Long-term potentiation in the dentate gyrus is induced preferentially on the positive phase of 0 rhythm," Brain Research, Elsevier, vol. 439, No. 1/2, Jan. 26, 1988, 7 pp.
Pfurtscheller et al., EEG Event-Related Desynchronization (ERD) and Event-Related Synchronizations (ERS), Chapter 45 Part VII, Evoked Potentials and Event-Related EEG Phenomena, Electroencephalography: Basic Principals, clinical applications and related fields., Lippincott, Williams and Wilkins, Sixth Edition, 2005, 14 pp.
Puil et al., "Quantification of Membrane Properties of trigeminal Root Ganglion Neurons in Guinea Pigs," Journal of Neurophyiology, vol. 55, No. 5, The American Physiological Society, May 1986, 22 pp.
Rizzuto et al., "Human neocortical oscillations exhibit theta phase differences between encoding and retrieval," NeuroImage, vol. 31, Science Direct, Elsevier, Mar. 15, 2006, 7 pp.
Rutishauser et al., "Human Memory Strength is Predicted by Theta-frequency phase-locking of single neurons," Nature Publishing Group, vol. 464, Apr. 8, 2010, 8 pp.
Sauseng et al., "What does phase information of oscillatory brain activity tell us about cognitive processes?," Science Direct, Elsevier Ltd., Neuroscience and Biobehavioral Reviews, Mar. 29, 2008, 13 pp.
Van Zaen et al., "Adaptive tracking of EEG oscillations," Journal of Neuroscience Methods, vol. 186, Elsevier, Oct. 23, 2009, 10 pp.
U.S. Appl. No. 17/077,805, by Medtronic, Inc. (Inventors: Jackson et al.), filed Oct. 22, 2020.

* cited by examiner

DETERMINATION OF THERAPY ELECTRODE LOCATIONS RELATIVE TO OSCILLATORY SOURCES WITHIN PATIENT

TECHNICAL FIELD

This disclosure generally relates to electrical stimulation therapy.

BACKGROUND

Medical devices may be external or implanted, and may be used to deliver electrical stimulation therapy to various tissue sites of a patient to treat a variety of symptoms or conditions such as chronic pain, tremor, Parkinson's disease, other movement disorders, epilepsy, urinary or fecal incontinence, sexual dysfunction, obesity, or gastroparesis. A medical device delivers electrical stimulation therapy via one or more leads that include electrodes located proximate to target locations associated with the brain, the spinal cord, pelvic nerves, peripheral nerves, or the gastrointestinal tract of a patent. For bipolar stimulation, the electrodes used for stimulation may be on one or more leads. For unipolar stimulation, the electrodes may be on one or more leads, and an electrode on a stimulator housing located remotely from the target site. It may be possible to use leadless stimulation using electrodes mounted on the stimulation housing. Electrical stimulation is used in different therapeutic applications, such as deep brain stimulation (DBS), spinal cord stimulation (SCS), pelvic stimulation, gastric stimulation, or peripheral nerve field stimulation (PNFS).

A clinician may select values for a number of programmable parameters in order to define the electrical stimulation therapy to be delivered by the implantable stimulator to a patient. For example, the clinician may select one or more electrodes for delivery of the stimulation, a polarity of each selected electrode, a voltage or current pulse amplitude, a pulse width, and a pulse frequency as stimulation parameters. A set of parameters, such as a set including electrode combination, electrode polarity, amplitude, pulse width, and pulse rate, may be referred to as a program in the sense that they define the electrical stimulation therapy to be delivered to the patient.

SUMMARY

This disclosure describes example techniques for determining which electrodes to use for therapy delivery. In some examples, electrodes to use for therapy delivery are those that are most proximate to an oscillatory signal source. The example techniques may include ways to determine which electrodes are most proximate to the oscillatory signal source.

For instance, the example techniques may include determining current source densities (CSDs) measured at each of a plurality of electrodes. The CSD measurements may be a time-varying voltage measurement. Therefore, there may be a technical problem in relying on an instantaneous CSD value to determine which electrodes to use for therapy delivery. This disclosure describes technical solutions to addressing problems with using instantaneous CSD values, where the technical solutions further have practical applications for selecting electrodes to use for delivering therapy.

In some examples, the disclosure describes techniques for aggregating multiple CSD measurements to generate an average level value indicative of the CSD at each of the electrodes. However, in aggregating the CSD measurements, phase information of the CSD measurements may be lost. Accordingly, this disclosure describes example techniques of determining phase-magnitude information for the CSD measurements. Based on the average level value (e.g., the aggregated CSD measurements) and phase-magnitude information of the CSD measurements, the example techniques provide for a more accurate measure of CSD and a more effective technique for selecting which electrodes to use for stimulation. Furthermore, for determining the CSD measurements, the example techniques may account for both horizontal and vertical differences between electrodes, and in some examples, patient anisotropy, providing a more accurate way to perform CSD measurements.

In one example, this disclosure describes a method comprising determining, for one or more electrodes of a plurality of electrodes, respective time-varying measurements of current source densities (CSDs), aggregating, for the one or more electrodes of the plurality electrodes, the respective time-varying measurements of the CSDs to generate respective average level values for the one or more electrodes of the plurality of electrodes, determining, for one or more electrodes of the plurality of electrodes, respective phase-magnitude representations of the time-varying measurements of the CSDs, wherein the respective phase-magnitude representations are indicative of respective magnitudes and phases of a particular frequency component of respective time-varying measurements of the CSDs and wherein the particular frequency component is a frequency component having a largest transform coefficient in a time-varying measurement of a CSD having a largest average level value, and generating information indicative of the respective average level values and respective phase-magnitude representations.

In one example, this disclosure describes a system comprising a memory configured to store electrical signal levels and processing circuitry. The processing circuitry is configured to determine, for one or more electrodes of a plurality of electrodes, respective time-varying measurements of current source densities (CSDs) based on the electrical signal levels, aggregate, for the one or more electrodes of the plurality electrodes, the respective time-varying measurements of the CSDs to generate respective average level values for the one or more electrodes of the plurality of electrodes, determine, for one or more electrodes of the plurality of electrodes, respective phase-magnitude representations of the time-varying measurements of the CSDs, wherein the respective phase-magnitude representations are indicative of respective magnitudes and phases of a particular frequency component of respective time-varying measurements of the CSDs, wherein the particular frequency component is a frequency component having a largest transform coefficient in a time-varying measurement of a CSD having a largest average level value, and generate information indicative of the respective average level values and respective phase-magnitude representations.

In one example, this disclosure describes a computer-readable storage medium comprising instructions that when executed cause one or more processors to determine, for one or more electrodes of a plurality of electrodes, respective time-varying measurements of current source densities (CSDs), aggregate, for the one or more electrodes of the plurality electrodes, the respective time-varying measurements of the CSDs to generate respective average level values for the one or more electrodes of the plurality of electrodes, determine, for one or more electrodes of the plurality of electrodes, respective phase-magnitude representations of the time-varying measurements of the CSDs, wherein the respective phase-magnitude representations are indicative of respective magnitudes and phases of a particular frequency component of respective time-varying measurements of the CSDs, wherein the particular frequency component is a frequency component having a largest transform coefficient in a time-varying measurement of a CSD having a largest average level value, and generate information indicative of the respective average level values and respective phase-magnitude representations.

The details of one or more examples of the techniques of this disclosure are set forth in the accompanying drawings and the description below. Other features, objects, and advantages of the techniques will be apparent from the description and drawings, and from the claims.

DETAILED DESCRIPTION

Figure 1:
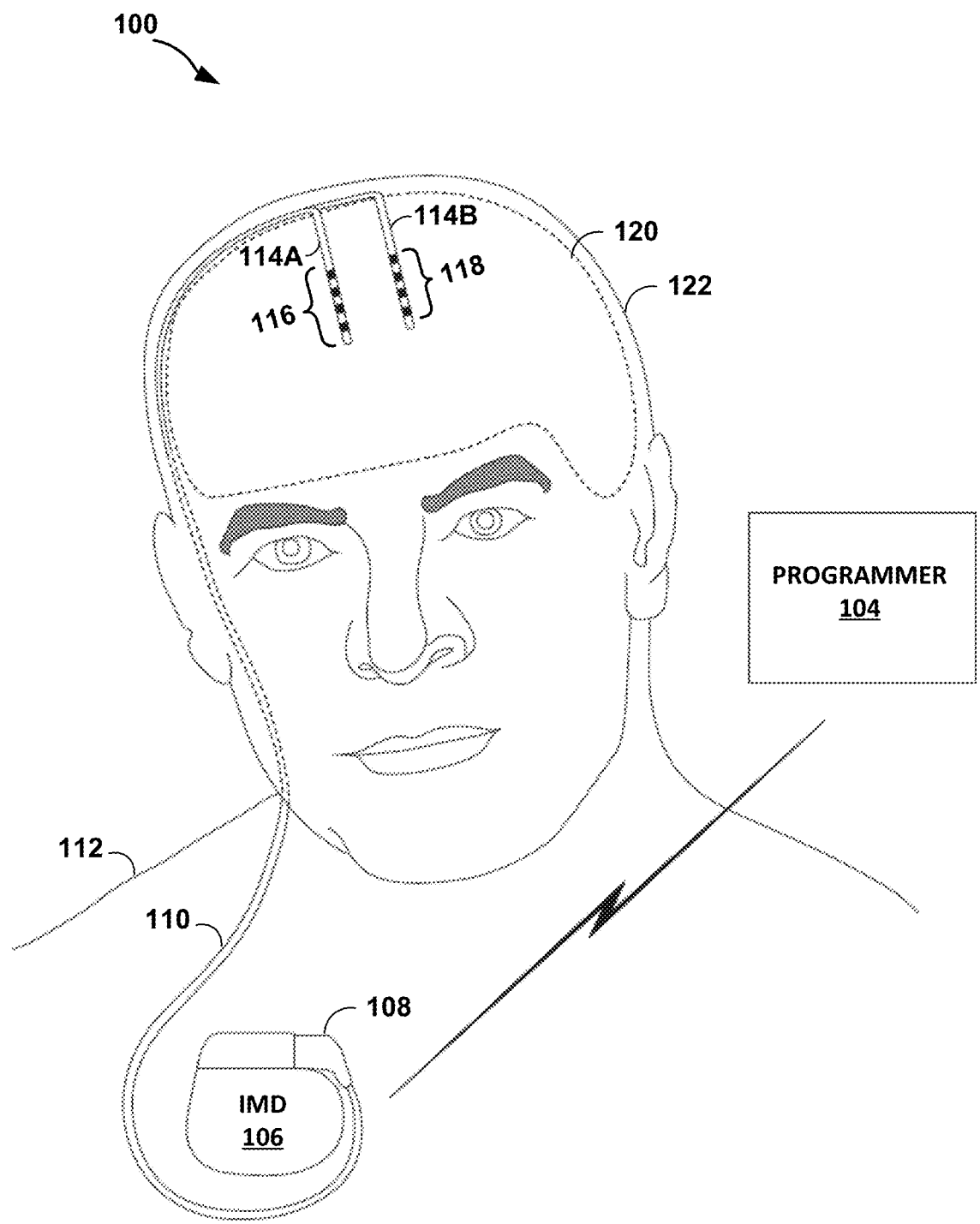
FIG. 1 is a conceptual diagram illustrating an example system that includes an implantable medical device (IMD) configured to deliver adaptive DBS to a patient according to an example of the techniques of the disclosure.

This disclosure describes example techniques to determine which electrodes are more proximate to an oscillatory signal source, relative to other electrodes. In one or more examples, an implantable medical device (IMD) determines a current source density (CSD) on each electrode. The CSD is a result of one or more oscillatory signal sources within a patient (e.g., within the brain of the patient). For example, the oscillatory signal sources can be considered to be current sources that output an oscillating current (e.g., time-varying current having an amplitude that changes over time and may be periodic but not limited to periodic time-varying current). The electrodes sense the oscillating current, which causes a voltage to develop on the electrodes relative to each other or a common ground. The CSD is indicative of the current density on an electrode due to the oscillatory signal sources, which is proportional to the amplitude of the voltage on the electrodes.

The electrodes having higher voltages, due to the current from the oscillatory signal sources, are more proximate to the oscillatory signal source, than electrodes having lower voltages, due to the current from the oscillatory signal sources. The electrodes more proximate to the oscillatory signal source may be better candidates for therapy delivery than other electrodes that are less proximate to the oscillatory signal source.

To determine a current source density on an electrode, the IMD may determine the differential voltage between the electrode and one or more neighboring electrodes (e.g., vertically neighboring and horizontally neighboring electrodes). In accordance with one or more examples, the IMD may scale the differential voltage of horizontally neighboring electrodes based on an angular horizontal distance between the horizontally neighboring electrodes. Also, the IMD may scale the differential voltage of vertically neighboring electrodes based on a vertical distance between the vertically neighboring electrodes. In this way, the IMD may account for positions of the electrodes as part of the CSD determination. For instance, IMD may divide the CSD determination into horizontal and vertical components that are separately scaled to provide a better measure of the CSD.

Furthermore, because the current from the oscillatory signal sources is a time-varying signal, the voltage formed at the electrodes is also a time-varying signal, and therefore, the voltages formed at the electrodes are time-varying measurements of the CSDs. Accordingly, an instantaneous measurement of the CSD of an electrode may not be indicative of the overall amplitude of the CSD because the instantaneous measurement of the CSD is a snapshot of the CSD and fails to account for the varying nature of the signal.

In one or more examples, the IMD may be configured to aggregate a time-series of CSD measurements, i.e., a CSD time-series, from each electrode into a single value for that electrode. For example, the IMD may be configured to aggregate the respective time-varying measurements of the CSDs to generate respective average level values for one or more electrodes of the plurality of electrodes (e.g., for electrode of the plurality of electrodes). One example way to aggregate the time-varying measurements of the CSDs is to determine the root-mean-square (RMS) value of the CSD for the one or more electrodes. Root-mean-square is one of many methods for quantifying an estimate related to energy or power of a signal, other options would include, but not be limited to, sum(abs(CSD(t))), sum(squared(CSD(t)), sqrt (sum(squared(CSD(t)-mean(CSD(t))))). In general, these measurements may be considered as average level values.

However, the average level values only provide information on the relative amplitudes of the CSD signals and neglects phase information that might be important for discriminating between different physiologically relevant sources of the signal. Accordingly, the IMD may be configured to determine, for the one or more electrodes of the plurality of electrodes (including each electrode of the plurality of electrodes), respective phase-magnitude representations of the time-varying measurements of the CSDs. As described in more detail, the respective phase-magnitude representations are indicative of respective magnitudes and phases of a particular frequency component of respective time-varying measurements of the CSDs. The particular frequency component may be chosen based on criteria relevant to the specific therapeutic application, such a known frequency band related to brain oscillations associated with a pathological state, as in the abnormal beta rhythm observed in the subthalamic nucleus of Parkinson's patients. The frequency component having a largest transform coefficient in a time-varying measurement of a CSD may be used as a phase reference, for example, by subtracting that component's phase from the components derived for of all other electrodes, making the phase reference relative to zero-phase.

In one or more examples, the IMD or a programmer may generate information indicative of the respective average level values (e.g., RMS values, as one non-limiting example) and respective phase-magnitude representations. A clinician may then determine which electrodes are most proximate to an oscillatory signal source based on the generated information. In one or more examples, the IMD or the programmer may determine which electrodes are most proximate to the oscillatory signal source based on the respective average values and the respective phase-magnitudes and generate information indicative of the determined electrodes. As described above, the electrodes that are most proximate to the oscillatory signal source tend to be the electrodes that should be used for stimulation (e.g., such as for Parkinson's patients). In some examples, electrodes that are most distal to the oscillatory signal source may be the electrodes that should be used for stimulation. In some examples, electrodes between the most distal and most proximate electrodes should be used for stimulation.

In this manner, the example techniques may generate information that can be used to more accurately determine which electrodes should be used for stimulation and more accurately determine one or more therapy parameters. For instance, with the average level values for the time-varying measurements of the CSD, there may be a more accurate determination of which electrodes have the highest CSD as compared to instantaneous measurements of the CSD. Also, with the phase-magnitude representation, it may be possible to determine whether oscillatory signal sources are operating as current sinks when others are current sources, or vice versa, effectively differentiating two or more regions of the local tissue, allowing the stimulation parameters to be selected accordingly to disrupt the signal generated by the oscillatory signal sources of interest. Such an approach may be beneficial for patterning or interleaving of stimulation across multiple electrodes. Furthermore, because the CSD measurements are divided into horizontal and vertical components, the example techniques may determine the time-varying measurements of the CSD with greater accuracy as compared to techniques that do not account for the vertical and horizontal distances between electrodes.

FIG. 1 is a conceptual diagram illustrating an example system 100 that includes an implantable medical device (IMD) 106 configured to deliver adaptive deep brain stimulation to a patient 112. DBS may be adaptive in the sense that IMD 106 may adjust, increase, or decrease the magnitude of one or more parameters of the DB S in response to changes in patient activity or movement, a severity of one or more symptoms of a disease of the patient, a presence of one or more side effects due to the DBS, or one or more sensed signals of the patient.

For instance, one example of system 100 is a bi-directional DBS system with capabilities to both deliver stimulation and sense intrinsic neuronal signals. System 100 provides for "closed-loop" therapy where IMD 106 may continuously monitor the state of certain biomarker signals and deliver stimulation according to pre-programmed routines based on the biomarker signals.

System 100 may be configured to treat a patient condition, such as a movement disorder, neurodegenerative impairment, a mood disorder, or a seizure disorder of patient 112. Patient 112 ordinarily is a human patient. In some cases, however, therapy system 100 may be applied to other mammalian or non-mammalian, non-human patients. While movement disorders and neurodegenerative impairment are primarily referred to herein, in other examples, therapy system 100 may provide therapy to manage symptoms of other patient conditions, such as, but not limited to, seizure disorders (e.g., epilepsy) or mood (or psychological) disorders (e.g., major depressive disorder (MDD), bipolar disorder, anxiety disorders, post-traumatic stress disorder, dysthymic disorder, and obsessive-compulsive disorder (OCD)). At least some of these disorders may be manifested in one or more patient movement behaviors. As described herein, a movement disorder or other neurodegenerative impairment may include symptoms such as, for example, muscle control impairment, motion impairment or other movement problems, such as rigidity, spasticity, bradykinesia, rhythmic hyperkinesia, nonrhythmic hyperkinesia, and akinesia. In some cases, the movement disorder may be a symptom of Parkinson's disease. However, the movement disorder may be attributable to other patient conditions.

Example therapy system 100 includes medical device programmer 104, implantable medical device (IMD) 106, lead extension 110, and leads 114A and 114B with respective sets of electrodes 116, 118. In the example shown in FIG. 1, electrodes 116, 118 of leads 114A, 114B are positioned to deliver electrical stimulation to a tissue site within brain 120, such as a deep brain site under the dura mater of brain 120 of patient 112. In some examples, delivery of stimulation to one or more regions of brain 120, such as the subthalamic nucleus, globus pallidus or thalamus, may be an effective treatment to manage movement disorders, such as Parkinson's disease. Some or all of electrodes 116, 118 also may be positioned to sense neurological brain signals within brain 120 of patient 112. In some examples, some of electrodes 116, 118 may be configured to sense neurological brain signals and others of electrodes 116, 118 may be configured to deliver adaptive electrical stimulation to brain 120. In other examples, all of electrodes 116, 118 are configured to both sense neurological brain signals and deliver adaptive electrical stimulation to brain 120. In some examples, unipolar stimulation may be possible where one electrode is on the housing of IMD 106 or at another position remote from the distal ends of leads 114A, 114B.

IMD 106 includes a therapy module (e.g., which may include processing circuitry, signal generation circuitry or other electrical circuitry configured to perform the functions attributed to IMD 106) that includes a stimulation generator configured to generate and deliver electrical stimulation therapy to patient 112 via a subset of electrodes 116, 118 of leads 114A and 114B, respectively. The subset of electrodes 116, 118 that are used to deliver electrical stimulation to patient 112, and, in some cases, the polarity of the subset of electrodes 116, 118, may be referred to as a stimulation electrode combination. As described in further detail below, the stimulation electrode combination can be selected for a particular patient 112 and target tissue site (e.g., selected based on the patient condition). The group of electrodes 116, 118 includes at least one electrode and can include a plurality of electrodes. In some examples, the plurality of electrodes 116 and/or 118 may have a complex electrode geometry such that two or more electrodes are located at different positions around the perimeter of the respective lead.

In some examples, the neurological signals sensed within brain 120 may reflect changes in electrical current produced by the sum of electrical potential differences across brain tissue. Examples of neurological brain signals include, but are not limited to, bioelectric signals generated from local field potentials (LFP) sensed within one or more regions of brain 120. Electroencephalogram (EEG) signal or an electrocorticogram (ECoG) signal are also examples of bioelectric signals. For example, neurons generate the bioelectric signals, and if measured at depth, the bioelectric signals are LFPs, if measured on the coretex, the bioelectric signals are EcoG signals, and if on scalp, the bioelectric signals are EEG signals. In this disclosure, the term "oscillatory signal source" is used to describe a signal source that generates bioelectric signals.

One example of the feature of interest (e.g., biomarker) within the LFPs is synchronized beta frequency band (13-33 Hz) LFP activity recorded within the sensorimotor region of the subthalamic nucleus (STN) in Parkinson's disease patients. The source of the LFP activity can be considered as an oscillatory signal source, within the brain of the patient, that outputs an oscillatory electrical voltage signal that is sensed by one or more of electrodes 116 and/or 118. The suppression of pathological beta activity (e.g., suppression or squelching of the signal component of the bioelectric signals generated from the LFP source that is within the beta frequency band) by both medication and DBS may correlate with improvements in the motor symptoms of patients who have Parkinson's disease.

In some examples, the neurological brain signals that are used to select a stimulation electrode combination may be sensed within the same region of brain 120 as the target tissue site for the electrical stimulation. As previously indicated, these tissue sites may include tissue sites within anatomical structures such as the thalamus, subthalamic nucleus or globus pallidus of brain 120, as well as other target tissue sites. The specific target tissue sites and/or regions within brain 120 may be selected based on the patient condition. Thus, in some examples, both a stimulation electrode combination and sense electrode combinations may be selected from the same set of electrodes 116, 118. In other examples, the electrodes used for delivering electrical stimulation may be different than the electrodes used for sensing neurological brain signals.

Electrical stimulation generated by IMD 106 may be configured to manage a variety of disorders and conditions. In some examples, the stimulation generator of IMD 106 is configured to generate and deliver electrical stimulation pulses to patient 112 via electrodes of a selected stimulation electrode combination. However, in other examples, the stimulation generator of IMD 106 may be configured to generate and deliver a continuous wave signal, e.g., a sine wave or triangle wave. In either case, a stimulation generator within IMD 106 may generate the electrical stimulation therapy for DBS according to a selected therapy program. In examples in which IMD 106 delivers electrical stimulation in the form of stimulation pulses, a therapy program may include a set of therapy parameter values (e.g., stimulation parameters), such as a stimulation electrode combination for delivering stimulation to patient 112, pulse frequency, pulse width, and a current or voltage amplitude of the pulses. As previously indicated, the electrode combination may indicate the specific electrodes 116, 118 that are selected to deliver stimulation signals to tissue of patient 112 and the respective polarities of the selected electrodes.

In some examples, electrodes 116, 118 may be radially-segmented DBS arrays (rDB SA) of electrodes. Radially-segmented DBS arrays refer to electrodes that are segmented radially along the lead. As one example, leads 114A and 114B may include a first set of electrodes arranged circumferentially around leads 114A and 114B that are all at the same height level on leads 114A and 114B (e.g., same axial position along length of leads 114A and 114B). Each of the electrodes in the first set of electrodes is a separate segmented electrode and form a level of radially-segmented array of electrodes. Leads 114A and 114B may include a second set of electrodes arranged circumferentially around leads 114A and 114B that are all at the same height level on leads 114A and 114B. Each of the electrodes in the first set of electrodes is a separate segmented electrode and form a level of radially-segmented array of electrodes. The rDBSA electrodes may be beneficial for directional stimulation and sensing.

The signal component in the beta frequency band is described as one example, and the techniques are applicable to other types of LFP activity. Furthermore, the example techniques are not limited to examples where electrodes 116, 118 are an rDB SA of electrodes. The example of using rDBSA of electrodes is described as a way of directional stimulation and sensing. However, the example techniques are also useable in examples where directional stimulation and sensing are not available or are not used. Moreover, there may be other ways of performing directional stimulation and sensing that do not require the use of an rDB SA of electrodes.

To suppress the signal component having the beta frequency band from the oscillatory signal source, IMD 106 may output an electrical stimulation signal that alters the way in which neurons of the oscillatory signal source produce signals. For example, the electrical stimulation either directly inhibits a certain neuronal population that includes the oscillatory signal source or excites one group of neurons which in turn suppresses another group of neurons (e.g., network effect). The stimulation may act on the neurons directly, and not necessarily on the signals that the neurons (e.g., oscillatory signal source) produces.

As described in more detail, algorithms may be used to determine the most proximate electrodes of electrodes 116 and 118 to the oscillatory signal source. In some examples, the electrodes of electrodes 116 and 118 that are most proximate to the oscillatory source tend to be the electrodes with which electrical stimulation should be delivered. In some examples, electrodes 116 and 118 that are most distal to the oscillatory signal source may be the electrodes that should be used for stimulation. In some examples, electrodes 116 and 118 between the most distal and most proximate electrodes should be used for stimulation. Hence, determining which electrodes 116 and 118 are most proximate and distal may be useful in determining which electrodes 116 and 118 to use for stimulation.

For instance, it may be easier to steer current to proximate electrodes to form the electrical field to impact the oscillatory signal source. Producing the appropriate electrical field from further away electrodes may require more power and can also result in stimulating more tissue other than the tissue of the oscillatory signal source.

Electrodes of electrodes 116 and 118 that are most proximate to the oscillatory signal source may be the electrodes having the highest current source density (CSD). For instance, electrodes of electrodes 116 and 118 that have the highest CSD are also the closest to the oscillatory signal source.

Because the oscillatory signal source outputs an oscillatory signal (e.g., time-varying signal), the voltages generated at electrodes 116 and 118 are also oscillatory. The CSD is determined based on the voltages at electrodes 116 and 118. Determining an instantaneous measurement of the voltage provides an instantaneous measurement of the CSD. However, an instantaneous measurement of the CSD may not reflect the actual measurement of the CSD. Accordingly, in example techniques described in this disclosure, IMD 106 may determine, for one or more electrodes of the plurality of electrodes 116 and 118, respective time-varying measurements of the CSD. Example techniques to determine the time-varying measurements of the CSD are described in more detail below. IMD 106 may aggregate the respective time-varying measurements of the CSDs to generate respective average level values for one or more electrodes of the plurality of electrodes 116 and 118 (e.g., determine a root-mean-square (RMS) value).

However, the average level value of the CSDs may lack information about the phase of the time-varying measurements of the CSDs. Accordingly, IMD 106 may be configured to determine respective phase-magnitude representations of the time-varying measurements of the CSDs. The respective phase-magnitude representations are indicative of the respective amplitudes of frequency components of the respective time-varying measurements of the CSDs at different phases. Example techniques to determine the phase-magnitude representations are described in more detail below. IMD 106 may generate information indicative of the respective average level values and respective phase-magnitude representations.

IMD 106 may be implanted within a subcutaneous pocket above the clavicle, or, alternatively, on or within cranium 122 or at any other suitable site within patient 112. Generally, IMD 106 is constructed of a biocompatible material that resists corrosion and degradation from bodily fluids. IMD 106 may comprise a hermetic housing to substantially enclose components, such as a processor, therapy module, and memory.

As shown in FIG. 1, implanted lead extension 110 is coupled to IMD 106 via connector 108 (also referred to as a connector block or a header of IMD 106). In the example of FIG. 1, lead extension 110 traverses from the implant site of IMD 106 and along the neck of patient 112 to cranium 122 of patient 112 to access brain 120. In the example shown in FIG. 1, leads 114A and 114B (collectively "leads 114") are implanted within the right and left hemispheres (or in just one hemisphere in some examples), respectively, of patient 112 in order to deliver electrical stimulation to one or more regions of brain 120, which may be selected based on the patient condition or disorder controlled by therapy system 100. The specific target tissue site and the stimulation electrodes used to deliver stimulation to the target tissue site, however, may be selected, e.g., according to the identified patient behaviors and/or other sensed patient parameters. For example, the target tissue site may be the location of the oscillatory signal source that generates the bioelectric signal having a signal component in the beta frequency band. The stimulation electrodes used to deliver stimulation to the target tissue site may be those that are most proximate to the oscillatory signal source, e.g., using the example techniques described in this disclosure. Alternatively, the stimulation electrodes used to deliver stimulation to the target tissue site may be those that are most distal to the oscillatory signal source, e.g. in order to avoid producing a side effect or to activate an inactive circuit. For example, gamma oscillations may occur due to over stimulation and therefore, it may be desirable to not output stimulation on electrodes that are proximate to the signal source of the gamma oscillations to reduce the over stimulation.

Other lead 114 and IMD 106 implant sites are contemplated. For example, IMD 106 may be implanted on or within cranium 122, in some examples. Leads 114A and 114B may be implanted within the same hemisphere or IMD 106 may be coupled to a single lead implanted in a single hemisphere, in some examples.

Existing lead sets include axial leads carrying ring electrodes disposed at different axial positions and so-called "paddle" leads carrying planar arrays of electrodes. Selection of electrode combinations within an axial lead, a paddle lead, or among two or more different leads presents a challenge to the clinician. In some examples, more complex lead array geometries may be used.

Although leads 114 are shown in FIG. 1 as being coupled to a common lead extension 110, in other examples, leads 114 may be coupled to IMD 106 via separate lead extensions or directly to connector 108. Leads 114 may be positioned to deliver electrical stimulation to one or more target tissue sites within brain 120 to manage patient symptoms associated with a movement disorder of patient 112. Leads 114 may be implanted to position electrodes 116, 118 at desired locations of brain 120 through respective holes in cranium 122. Leads 114 may be placed at any location within brain 120 such that electrodes 116, 118 are capable of providing electrical stimulation to target tissue sites within brain 120 during treatment. For example, electrodes 116, 118 may be surgically implanted under the dura mater of brain 120 or within the cerebral cortex of brain 120 via a burr hole in cranium 122 of patient 112, and electrically coupled to IMD 106 via one or more leads 114.

In the example shown in FIG. 1, electrodes 116, 118 of leads 114 are shown as ring electrodes. Ring electrodes may be used in DBS applications because ring electrodes are relatively simple to program and are capable of delivering an electrical field to any tissue adjacent to electrodes 116, 118. In other examples, electrodes 116, 118 may have different configurations. For example, at least some of the electrodes 116, 118 of leads 114 may have a complex electrode array geometry that is capable of producing shaped electrical fields. The complex electrode array geometry may include multiple electrodes (e.g., partial ring or segmented electrodes) around the outer perimeter of each lead 114, rather than one ring electrode. In this manner, electrical stimulation may be directed in a specific direction from leads 114 to enhance therapy efficacy and reduce possible adverse side effects from stimulating a large volume of tissue.

In some examples, a housing of IMD 106 may include one or more stimulation and/or sensing electrodes. In some examples, leads 114 may have shapes other than elongated cylinders as shown in FIG. 1. For example, leads 114 may be paddle leads, spherical leads, bendable leads, or any other type of shape effective in treating patient 112 and/or minimizing invasiveness of leads 114.

IMD 106 includes a memory to store a plurality of therapy programs that each define a set of therapy parameter values. In some examples, IMD 106 may select a therapy program from the memory based on various parameters, such as sensed patient parameters and the identified patient behaviors. IMD 106 may generate electrical stimulation based on the parameters of the selected therapy program to manage the patient symptoms associated with a movement disorder.

External programmer 104 wirelessly communicates with IMD 106 as needed to provide or retrieve therapy information. Programmer 104 is an external computing device that the user, e.g., a clinician and/or patient 112, may use to communicate with IMD 106. For example, programmer 104 may be a clinician programmer that the clinician uses to communicate with IMD 106 and program one or more therapy programs for IMD 106. Alternatively, programmer 104 may be a patient programmer that allows patient 112 to select programs and/or view and modify therapy parameters. The clinician programmer may include more programming features than the patient programmer. In other words, more complex or sensitive tasks may only be allowed by the clinician programmer to prevent an untrained patient from making undesirable changes to IMD 106.

When programmer 104 is configured for use by the clinician, programmer 104 may be used to transmit initial programming information to IMD 106. This initial information may include hardware information, such as the type of leads 114 and the electrode arrangement, the position of leads 114 within brain 120, the configuration of electrode array 116, 118, initial programs defining therapy parameter values, and any other information the clinician desires to program into IMD 106. Programmer 104 may also be capable of completing functional tests (e.g., measuring the impedance of electrodes 116, 118 of leads 114).

The clinician may also store therapy programs within IMD 106 with the aid of programmer 104. During a programming session, the clinician may determine one or more therapy programs that may provide efficacious therapy to patient 112 to address symptoms associated with the patient condition, and, in some cases, specific to one or more different patient states, such as a sleep state, movement state or rest state. For example, the clinician may select one or more stimulation electrode combinations with which stimulation is delivered to brain 120. During the programming session, the clinician may evaluate the efficacy of the specific program being evaluated based on feedback provided by patient 112 or based on one or more physiological parameters of patient 112 (e.g., muscle activity, muscle tone, rigidity, tremor, etc.). Alternatively, identified patient behavior from video information may be used as feedback during the initial and subsequent programming sessions. Programmer 104 may assist the clinician in the creation/identification of therapy programs by providing a methodical system for identifying potentially beneficial therapy parameter values.

However, as described in this disclosure, in some examples, IMD 106 or programmer 104 (e.g., a medical device), alone or in combination, may automatically determine electrode configuration and therapy parameters. For example, the medical device may determine which electrodes to use for stimulation based on which electrodes are most proximate to the oscillatory signal source. In some examples, programmer 104 may output information indicating the selected electrode configuration for stimulation and the determined stimulation amplitude or other therapy parameter for the clinician or physician to review and confirm before IMD 106 delivers therapy via the selected electrode configuration with the determined stimulation amplitude. In some examples, the example techniques may be performed in a cloud computing environment where computing devices are distributed in a cloud computing system and the example techniques are performed in the distributed computing devices of the cloud computing system.

Programmer 104 may also be configured for use by patient 112. When configured as a patient programmer, programmer 104 may have limited functionality (compared to a clinician programmer) in order to prevent patient 112 from altering critical functions of IMD 106 or applications that may be detrimental to patient 112. In this manner, programmer 104 may only allow patient 112 to adjust values for certain therapy parameters or set an available range of values for a particular therapy parameter.

Programmer 104 may also provide an indication to patient 112 when therapy is being delivered, when patient input has triggered a change in therapy or when the power source within programmer 104 or IMD 106 needs to be replaced or recharged. For example, programmer 104 may include an alert LED, may flash a message to patient 112 via a programmer display, generate an audible sound or somatosensory cue to confirm patient input was received, e.g., to indicate a patient state or to manually modify a therapy parameter.

Therapy system 100 may be implemented to provide chronic stimulation therapy to patient 112 over the course of several months or years. However, system 100 may also be employed on a trial basis to evaluate therapy before committing to full implantation. If implemented temporarily, some components of system 100 may not be implanted within patient 112. For example, patient 112 may be fitted with an external medical device, such as a trial stimulator, rather than IMD 106. The external medical device may be coupled to percutaneous leads or to implanted leads via a percutaneous extension. If the trial stimulator indicates DBS system 100 provides effective treatment to patient 112, the clinician may implant a chronic stimulator within patient 112 for relatively long-term treatment.

Although IMD 106 is described as delivering electrical stimulation therapy to brain 120, IMD 106 may be configured to direct electrical stimulation to other anatomical regions of patient 112. Further, an IMD may provide other electrical stimulation such as spinal cord stimulation to treat a movement disorder or pelvic floor stimulation.

According to the techniques of the disclosure, a medical device (e.g., IMD 106 or programmer 104) of system 100 may be configured to determine time-varying measurements of CSDs. One example way to determine the CSD for respective electrodes is based on voltage differences of adjacent electrodes. For example, IMD 106 may determine CSD values based on the voltage differences between the adjacent electrodes. In some examples, the CSD values may be the second spatial difference of voltage difference along the electrodes. Each of the second spatial difference of voltage differences may be a difference between the voltage differences. In other words, in some examples, the CSD values may be the differences between the voltage differences along the lead. In a more specific example, the two CSD values for a four-electrode system would be $(V_1-V_2)-(V_2-V_3)$ and $(V_2-V_3)-(V_3-V_4)$.

For example, the equation to determine the CSD is as follows.

$$\sum_{i=1}^{3}\left(\frac{\partial \sigma_{ii}}{\partial x_i} \cdot \frac{\partial \varphi}{\partial x_i} + \sigma_{ii} \cdot \frac{\partial^2 \varphi}{\partial x_i^2}\right) = -I$$

In the above equation, i represents the index of the dimension (e.g., x, y, or z in Cartesian space), $x_i$ represents one of the dimensions (viz. x, y, or z in Cartesian space), $\sigma_{ii}$ represents the diagonal components of the conductance tensor corresponding to dimension index i, $\varphi$ represents the voltage signal of interest (e.g., voltage at electrodes 116 and 118), and I represents the current (e.g., the CSD). If a net current is coming out of neural tissue in the vicinity of the electrode, a current source is registered and I is positive, and if the current is moving into the neural tissue in the vicinity of the electrode, a current sink results, and I is negative.

As an approximation, it is often assumed that the conductivity of the tissue is isotropic and does not change appreciably in the spatial vicinity of the electrodes. This yields a simplified equation as follows.

$$I = -\sigma \sum_{i=1}^{3} \left( \frac{\partial^2 \varphi}{\partial x_i^2} \right)$$

Since the signal of interest, $\varphi(t)$, which is the voltage at one of electrodes 116 and 118 and is a time-varying signal, can be differentially sensed between adjacent pairs of equidistant electrodes, the second-order derivative of $\varphi(t)$ can be approximated as follows.

$$\frac{\partial^2 \varphi}{\partial x_i^2} \approx \frac{\Delta \varphi(a,b)}{\Delta x_i(a,b)} - \frac{\Delta \varphi(b,c)}{\Delta x_i(b,c)}$$

In the above equation, a, b, and c are adjacent electrodes, $\Delta x_i(a,b)$ is the distance between electrode a and b, $\Delta x_i(b,c)$ is the distance between electrode b and c, $\Delta \varphi(a,b)$ is the difference in the signal between electrode a and b, and $\Delta \varphi(b,c)$ is the difference in the signal between electrode b and c. Distance between electrodes could be measured from a predetermined point on an edge of one electrode to predetermined point on an edge of an adjacent electrode (such as the closest two points existing between adjacent electrodes.) Alternatively, distance could be the average spacing existing between the points of closest edges of adjacent electrodes. In some examples, the distance may be the distance between center points of the electrodes. In general, distance may be indicative of spacing between electrodes. As described in more detail, to isolate certain frequency markers (e.g., beta band), it may be possible to filter the signal of interest, $\varphi(t)$, or determine a transform (e.g., Fourier transform) of the signal of interest, $\varphi(t)$, and determine the frequency of interest from the transformed signal.

The above equations provide the CSD values in Cartesian coordinates. The following provides the derivation of the CSD equation in cylindrical coordinates system for use with leads that have cylindrical geometries, such as a segmented DBS lead.

As noted above, the equation for the CSD on an electrode is:

$$\sum_{i=1}^{3} \left( \frac{\partial \sigma_{ii}}{\partial x_i} \cdot \frac{\partial \varphi}{\partial x_i} + \sigma_{ii} \cdot \frac{\partial^2 \varphi}{\partial x_i^2} \right) = -I.$$

For leads with radially-distributed electrodes, $\nabla \cdot (\sigma \nabla \varphi) = -I$ can be expanded in terms of cylindrical coordinates. Assuming the conductivity matrix is expressed in cylindrical coordinates, the result may be $$\sigma = \begin{pmatrix} \sigma_{rr} & 0 & 0 \\ 0 & \sigma_{\theta\theta} & 0 \\ 0 & 0 & \sigma_{zz} \end{pmatrix}$$

Note that the gradient in this coordinate system is $$\nabla = \left( \frac{\partial}{\partial r}, \frac{1}{r} \frac{\partial}{\partial \theta}, \frac{\partial}{\partial z} \right),$$

and so $$-I = \nabla \cdot \left( \sigma_{rr} \frac{\partial \varphi}{\partial r}, \frac{\sigma_{\theta\theta}}{r} \frac{\partial \varphi}{\partial \theta}, \sigma_{zz} \frac{\partial \varphi}{\partial z} \right)$$

Which can be written in terms of the cylindrical coordinate basis vectors: $\hat{e}_r$ $\hat{e}_\theta$ $\hat{e}_z$ $$-I = \left( \hat{e}_r \frac{\partial}{\partial r} + \hat{e}_\theta \frac{1}{r} \frac{\partial}{\partial \theta} + \hat{e}_z \frac{\partial}{\partial z} \right) \cdot \left( \sigma_{rr} \frac{\partial \varphi}{\partial r} \hat{e}_r + \frac{\sigma_{\theta\theta}}{r} \frac{\partial \varphi}{\partial \theta} \hat{e}_\theta + \sigma_{zz} \frac{\partial \varphi}{\partial z} \hat{e}_z \right)$$

In the above equations, r is the radius from the center of the lead, and θ is the angular position around the lead. Expanding and distributing the derivative, the partial derivatives of the basis vectors are nearly all zero except in two cases:

$$\frac{\partial \hat{e}_r}{\partial \theta} = \hat{e}_\theta \text{ and } \frac{\partial \hat{e}_\theta}{\partial \theta} = -\hat{e}_r.$$

Distributing the partial derivatives and applying the product rule:

$$-I = \hat{e}_r \cdot \left( \frac{\partial}{\partial r} \left( \sigma_{rr} \frac{\partial \varphi}{\partial r} \right) \hat{e}_r + \frac{\partial}{\partial r} \left( \frac{\sigma_{\theta\theta}}{r} \frac{\partial \varphi}{\partial \theta} \right) \hat{e}_\theta + \frac{\partial}{\partial r} \left( \sigma_{zz} \frac{\partial \varphi}{\partial z} \right) \hat{e}_z \right) +$$
$$\hat{e}_\theta \frac{1}{r} \cdot \left( \frac{\partial}{\partial \theta} \left( \sigma_{rr} \frac{\partial \varphi}{\partial r} \right) \hat{e}_r + \sigma_{rr} \frac{\partial \varphi}{\partial r} \hat{e}_\theta + \right.$$
$$\frac{\partial}{\partial \theta} \left( \frac{\sigma_{\theta\theta}}{r} \frac{\partial \phi}{\partial \theta} \right) \hat{e}_\theta - \frac{\sigma_{\theta\theta}}{r} \frac{\partial \varphi}{\partial \theta} \hat{e}_r + \frac{\partial}{\partial \theta} \left( \sigma_{zz} \frac{\partial \varphi}{\partial z} \right) \hat{e}_z \right) +$$
$$\hat{e}_z \cdot \left( \frac{\partial}{\partial z} \left( \sigma_{rr} \frac{\partial \varphi}{\partial r} \right) \hat{e}_r + \frac{\partial}{\partial z} \left( \frac{\sigma_{\theta\theta}}{r} \frac{\partial \varphi}{\partial \theta} \right) \hat{e}_\theta + \frac{\partial}{\partial z} \left( \sigma_{zz} \frac{\partial \varphi}{\partial z} \right) \hat{e}_z \right)$$

Assuming that $\sigma_{ii}$, $\varphi$, and $-I$ are to be expressed in cylindrical coordinates, and since the basis vectors are orthogonal, many terms equal zero when with application of the dot product:

$$-I = \frac{\partial}{\partial r} \left( \sigma_{rr} \frac{\partial \varphi}{\partial r} \right) + \frac{1}{r} \left( \sigma_{rr} \frac{\partial \varphi}{\partial r} + \frac{\partial}{\partial \theta} \left( \frac{\sigma_{\theta\theta}}{r} \frac{\partial \varphi}{\partial \theta} \right) \right) + \frac{\partial}{\partial z} \left( \sigma_{zz} \frac{\partial \varphi}{\partial z} \right)$$

If assumed that the conductivity of the tissue does not change appreciably in the vicinity of the electrode, then $\sigma_{rr}$, $\sigma_{\theta\theta}$, and $\sigma_{zz}$ constant and this can be rewritten:

$$-I = \frac{\sigma_{rr}}{r} \frac{\partial}{\partial r} \left( r \frac{\partial \varphi}{\partial r} \right) + \frac{\sigma_{\theta\theta}}{r^2} \frac{\partial^2 \varphi}{\partial \theta^2} + \sigma_{zz} \frac{\partial^2 \varphi}{\partial z^2}$$

For examples where the radius r is not changing, such as in leads 114A and 114B, the above equation can be further simplified to the following.

$$-I = \frac{\sigma_{\theta\theta}}{r^2} \frac{\partial^2 \varphi}{\partial \theta^2} + \sigma_{zz} \frac{\partial^2 \varphi}{\partial z^2}$$

The above equation could be used for customizing CSD to be measured or estimated using relative or absolute anisotropy of the local tissue impedance to provide individualized or target-specific CSD estimates. Also, if the values of the conductivity tensor are assumed to be all equal (e.g., $\sigma_{ii}=\sigma$), meaning there is an isotropic medium, then the above equation can be further simplified as follows.

$$-I = \sigma \left( \frac{1}{r^2} \frac{\partial^2 \varphi}{\partial \theta^2} + \frac{\partial^2 \varphi}{\partial z^2} \right)$$

In the above equations, for a fixed, regular angular and vertical spacing of a segmented lead, $\partial\Theta=\Delta\Theta$ and $\partial z=\Delta z$. For example, $\Delta\Theta$ represents the horizontal distance (e.g., angular distance) between two horizontally neighboring electrodes, and $\Delta z$ represents a vertical distance between two vertically neighboring electrodes. For differential recordings $\Delta V_{i,i+1}$, where i is the reference (anode) and i+1 is the cathode, differences between adjacent bipolar recordings $\Delta V_{i+1,i+2} - \Delta V_{i,i+1}$ can be used to approximate a second derivative as follows.

$$\partial \varphi \cong \Delta V_{i,i+1}(t)$$

$$\partial^2 \varphi \cong \Delta V_{i+1,i+2}(t) - \Delta V_{i,i+1}(t)$$

For example, IMD 106 may be configured to determine bipolar measurements of the voltages at electrodes 116 and 118. A bipolar measurement means that IMD 106 determines a voltage across pairs of electrodes rather than with respect to ground. The bipolar measurement is represented by $\Delta V_{i,i+1}$, where i is the reference (anode) and i+1 is the cathode. The bipolar measurement represents a first derivative, and the difference between two simultaneously recorded adjacent bipolar pairs is an estimate of the second derivative. For example, $\Delta V_{i+1,i+2} - \Delta V_{i,i+1}$ is an estimate of the second derivative, and can be rewritten as follows: $(V_{i+1}-V_{i+2})-(V_i-V_{i+1})$. This equation can be used as the second derivative when determining the CSD for the electrode i. Accordingly, a minimum of two adjacent pairs of electrodes of electrodes 116 and 118 may be needed to determine whether the electrode is proximate to an oscillatory signal source (e.g., an oscillatory signal source that is sinking current or an oscillatory signal source that is sourcing current).

Based on the above, the equation for the CSD value can be written as follows.

$$I = -\left( \frac{\sigma_{\theta\theta}}{r^2} \frac{\Delta V_{i,i+1}(t) - \Delta V_{i-1,i}(t)}{(\Delta \theta)^2} + \sigma_{zz} \frac{\Delta V_{j,j+1}(t) - \Delta V_{j-1,j}(t)}{(\Delta z)^2} \right)$$

$$= -(\sigma_{\theta\theta} A_i(t) + \sigma_{zz} Z_j(t))$$

The above equation can be simplified for the isotropic case as follows.

$$I_i(t) = -\sigma[A_i(t) + Z_i(t)], \text{ where } A_i(t) = \left( \frac{1}{r^2} \frac{\Delta V_{i,i+1}(t) - \Delta V_{i-1,i}(t)}{(\Delta \theta)^2} \right)$$

$$Z_j(t) = \left( \frac{\Delta V_{j,j+1}(t) - \Delta V_{j-1,j}(t)}{(\Delta z)^2} \right)$$

In the above equation, the time-varying CSD value (e.g., $I_i(t)$) is computed by separating the measurements of the horizontal components and the vertical components. For instance, $A_i(t)$ is the measurement of the horizontal component of the CSD, and $Z_i(t)$ is the measurement of the vertical component of the CSD. Note that for greatest accuracy, $A_i(t)$ and $Z_i(t)$ are typically simultaneously measured. In the above equation, there is only one value for the tissue impedance anisotropy (e.g., $\sigma$). However, in some examples, the conductivity tensor can be empirically determined, such that the value for the tissue impedance anisotropies could be separated out (e.g., there could be a separate value for $\sigma_{11}$, $\sigma_{22}$, and $\sigma_{33}$). Further, these could be relative or normalized values, as often, the practical application may only require relative CSD values.

Another computation simplification that can be made for contacts with equal vertical and horizontal spacing h is that the denominators $\Delta\theta^2$ and $\Delta z^2$ of can be replaced with the spacing h, eliminating the squaring step, since there is interest in looking at relative magnitudes of the CSD across electrodes.

As described above, IMD 106 may be configured to determine, for one or more electrodes of the plurality of electrodes 116 and 118, respective time-varying measurements of CSDs. To perform such operations, IMD 106 may be configured to determine, for one or more electrodes of the plurality of electrodes 116 and 118, respective first time-varying measurements (e.g., $A_i(t)$ based on second-order voltage differences between two electrodes that horizontally neighbor each electrode (e.g., $\Delta V_{i,i+1}(t)-\Delta V_{i-1,i}(t)$) and a horizontal distance between the two horizontally neighboring electrodes (e.g., $\Delta\theta$). IMD 106 may also be configured to determine, for one or more electrodes of the plurality of electrodes 116 and 118, respective second time-varying measurements (e.g., $Z_i(t)$) based on second-order voltage differences between two electrodes that vertically neighbor each electrode (e.g., $\Delta V_{j,j+1}(t)-\Delta V_{j-1,j}(t)$) and a vertical distance between the two vertically neighboring electrodes (e.g., $\Delta z$). Distances between two adjacent electrodes may be measured in various ways, as discussed above. IMD 106 may determine respective time-varying measurements of the CSDs based on the respective first time-varying measurements and the second time-varying measurements (e.g., $I_i(t)=-\sigma[A_i(t)+Z_i(t)]$).

In some examples, to determine the first time-varying measurement (e.g., $A_i(t)$), IMD 106 may scale $(\Delta V_{i,i+1}(t)-\Delta V_{i-1,i}(t))/(\Delta\Theta)^2$ by a radius of a lead that includes the respective electrodes. The radius of the lead is r, and scaling may include multiplying $(\Delta V_{i,i+1}(t)-\Delta V_{i-1,i}(t))/(\Delta\Theta)^2$ by $1/r$. Also, in some examples, IMD 106 may scale at least one of first time-varying measurement (e.g., $A_i(t)$) or the second time-varying measurement (e.g., $Z_i(t)$) based on an anisotropy of local tissue impedance of the two horizontally neighboring electrodes or the two vertically neighboring electrodes. In the above example, $\sigma$ represents the isotropy of local tissue impedance and may be assumed to be the same for the horizontally neighboring electrodes and the vertically neighboring electrodes, alternatively, as shown earlier, anatomical variation or electrode characteristics may result in tissue impedance that may be different for the horizontally neighboring electrodes and the vertically neighboring electrodes.

In one or more examples, IMD 106 separately determines the time-varying measurement for the horizontal component (e.g., $A_i(t)$) and the time-varying measurement for the vertical component (e.g., $Z_i(t)$). For example, $A_i(t)$ is based on the horizontal distance between electrodes (e.g., $\Delta\Theta$), and $Z_i(t)$ is based on the vertical distance between electrodes (e.g., $\Delta z$). By separating the horizontal and vertical components (e.g., determining the horizontal and vertical components based on horizontal and vertical distances, respectively), the time-varying measurement of the CSD may be more accurate as compared to other techniques that do not separate out the horizontal and vertical components, and only rely on voltage differences between neighboring electrodes.

In some examples, IMD 106 may perform filtering to isolate time-domain representations of a biomarker signal of interest (e.g., matched-filter based, wavelet, or other signal processing techniques). As one example, a band pass filter from 15 to 30 Hz could be used to isolate beta oscillations, which are a putative biomarker for akinetic symptoms of Parkinson's disease.

It should be understood that there may be various signal processing techniques that may be applied to isolate a particular band of interest. As one example, IMD 106 may determine the second-derivative of the voltage measurements (e.g., $\Delta V_{i,i+1}(t) - \Delta V_{i-1,i}(t)$) and $\Delta V_{j,j+1}(t) - \Delta V_{j-1,j}(t)$). IMD 106 may then determine $A_i(t)$ and $Z_i(t)$, and then filter $A_i(t)$ and $Z_i(t)$ for the biomarker signal of interest (e.g., filter to 15 Hz to 30 Hz). As another example, IMD 106 may first filter the voltage measurements, and then determine the second derivative of the voltage measurements. Based on the second derivative of the voltage measurements, generated from the filtered voltage measurements, IMD 106 may determine $A_i(t)$ and $Z_i(t)$. Although voltage measurements are described, the example techniques may be extended to other types of electrical signal levels as well (e.g., current measurements).

In the above examples, the time-domain filtering is utilized (e.g., bandpass filter). However, the techniques are not so limited. For example, rather than performing operations in the time-domain, IMD 106 may perform operations in the frequency-domain. For instance, IMD 106 may apply a Fourier transform (e.g., fast Fourier transform (FFT)) to the electrical signal levels (e.g., voltage measurements) to determine the amplitude of frequency components in the range of 15 Hz to 30 Hz. For the frequency components in the range of 15 Hz to 30 Hz, IMD 106 may determine the values of the horizontal component and the vertical component; however, these measurements would be in the frequency domain instead of the time-domain. For instance, in addition to or instead of determining $A_i(t)$ and $Z_i(t)$, IMD 106 may determine the MO and $Z_i(f)$ as frequency-varying values. In other words, $A_i(f)$ and $Z_i(f)$ are the FFT of $A_i(t)$ and $Z_i(t)$ respectively. There may be various instances in the processing algorithm where a time-domain filter or a transform from the time-domain to the frequency-domain can occur, and the example techniques are applicable to the different instances of where filtering or transforming occurs.

In some examples, IMD 106 may be configured to output the values of the computed time-varying CSD values (e.g., $I_i(t)$) to programmer 104, and programmer 104 may display information that assists with visualizing the CSD across electrodes. For example, programmer 104 may display a graphical time-varying signal representing the CSD for the electrodes. The visualization could be mapped to the electrode for a view that does not require imaging or lead targeting with orientation markers for the oscillatory signal source. In some examples, the visualization could incorporate electrode mapping with respect to local representations, imaging, or atlas segmentations of the tissue surrounding leads 114A and 114B. For example, the visualization would show the electrodes of electrodes 116 and 118, surrounding tissue, and the time-varying CSD values.

In some examples, the CSD values may be mapped to the center or shared electrode of a pair of simultaneous bipolar recordings for 1-D arrays or quadruplet of bipolar recordings for 2-D arrays (e.g., cylindrical or paddle arrays). For example, the CSD values may be slightly different at different points on an electrode, and in some examples, the CSD values may be considered as the CSD value at the center of the electrode. As another example, in determining the bipolar voltage measurements for determining the CSD values, it may be possible to couple two or more electrodes together so that the impedance for the electrodes is the same. In such examples, the CSD values may be considered to be a center point of the electrodes that are coupled together (e.g., the centroid of the coupled electrodes). In some cases, if measuring between a ring electrode and a segmented electrode, there may be impedance mismatch and therefore improper measurements.

In some examples, it may be possible to couple all segmented electrodes at the same axial level so that the electrodes coupled together are equivalent to a ring electrode. For example, a switch may be used to short the segment electrodes in the same axial level together (e.g., ganging segmented electrodes), measure signals between rings (e.g., between a true ring and the ring formed by the ganged electrodes), and using these signals to select a particular row. The electrode segments may then be "unganged," for instance, by the switch un-shorting the segment electrodes. In some examples, CSD values may be measured between the unganged electrodes.

In some examples, IMD 106 may gang the electrodes in a row and use the techniques described in this disclosure to pick one of the middle rows of segmented electrodes with the ganged electrodes. IMD 106 may un-gang the electrodes, and re-measure using the techniques described in this disclosure, and select one or more segmented electrodes within the selected row to use for therapy delivery. Ganging and un-ganging electrodes is one example and should not be considered limiting. In some examples, the ganged electrodes may be used to deliver therapy with an actual ring electrode.

As described, the CSD is a time-varying value. Displaying or visualizing time-varying values may be complicated and possibly difficult for the clinician or patient to comprehend. Providing an instantaneous value for the CSD may not be sufficient for the clinician or patient to understand which electrodes 116 and 118 are proximate to the oscillatory signal source because the instantaneous value of the CSD is a snap-shot value for that instant and does not provide sufficient information about how the CSD values vary over time.

Therefore, in one or more examples, IMD 106 may be configured to aggregate the time-varying values of the CSD. There may be various ways in which IMD 106 may aggregate the time-varying values of the CSD. As one example, IMD 106 may average relative CSD amplitude across electrodes, based on magnitude in the frequency domain for frequencies of interest, or on a phase/amplitude-based ranking.

There may be certain benefits with presenting the aggregated time-varying values of the CSD with normalized values, rather than just based on ranking or absolute values.

For example, raw aggregated CSD values (e.g., average level values determined from RMS) may result in scales that make it difficult to distinguish important differences between electrodes and ranking may over accentuate differences between electrodes with very similar CSD values. Accordingly, there may be benefits to normalizing the CSD values such that electrodes with similar high or low values can be seen as such. For example, two adjacent electrodes may be nearly equidistant from a very strong signal source, with minute differences in CSD between the two, due largely to noise, while the next closest electrode may have a much smaller CSD. Ranking would assign incremental differences between the three, which may obscure the fact that two are nearly the same. However, an absolute scale may not be so informative where relative differences are desired. So, normalization, would preserve the relative comparisons, while making particularly high or low CSD electrodes stand out from the average.

In some examples, IMD 106 may determine phase/amplitude mapping. In phase/amplitude mapping, IMD 106 may determine a root-mean-square (RMS) value, where the RMS value is representative of the average level values of the CSDs for one or more of electrodes 116 and 118. In addition, IMD 106 may determine the phase-magnitude representations for each of electrodes 116 and 118. The phase-magnitude representation may be indicative of respective amplitudes of frequency components of the respective time-varying measurements of the CSDs at different phases.

For instance, the average level values (e.g., based on RMS or some of other example techniques) may provide a value that represents the time-varying CSD values. However, in average level values, information about the phase of the time-varying CSD values may be lost. Phase information may be useful because the phase information differentiates between tissue regions acting as oscillatory signal sources (e.g., outputting current) or as sinks (e.g., receiving current). For example, based on a differential phase measurement (e.g., phase of signals at a first electrode relative to some baseline phase), it may be possible to determine that tissue regions around two different electrodes have signals with phases that are 180-degree different, which means that one tissue region is acting as the signal source and another is acting as the signal sink. By using a circular map for phase information and mapping opacity to average level values may yield strong contrast between out-of-phase signal generators (e.g., oscillatory signal sources that are sources and oscillatory signal sources that are sinks).

The above example techniques of generating visualization information (e.g., graphical information) is one example of information that IMD 106 may generate and then cause programmer 104 to display. However, the techniques described in this disclosure are not so limited. In some examples, IMD 106 may not provide any graphical visualization information. Rather, based on the phase-magnitude information, IMD 106 may generate data that lists the average level value for the CSD and generate data indicating whether an oscillatory signal source is a current source or a current sink. As another example, IMD 106 may determine which electrodes 116 and 118 are proximate, distal, or in between proximate and distal electrodes to the oscillatory signal source (e.g., based on the average level values of the CSD values and the phase-magnitude representation), and generate data indicating which electrodes 116 and 118 are proximate (e.g., "closer to"), distal (e.g., "farther away from"), or in between proximate and distal electrodes to the oscillatory signal source. In one or more examples, electrodes 116 and 118 that are proximate may be electrodes that are closer to the oscillation source or sink, and electrodes 116 and 118 that are distal may be electrodes that are farther away from the oscillation source or sink.

In some examples, IMD 106 may automatically generate the above example information. Further, in some examples, IMD 106 may be configured to change stimulation setting on electrodes in response to generating the above example information (e.g., electrodes that are proximate, distal, or in between and whether tissue near the electrodes is acting is a signal source or sink). The changes may be in an adaptive manner to target changes in the tissue acting like signal sources or sinks.

As described above, IMD 106 may be configured to aggregate the respective time-varying measurements of the CSDs to generate respective average level values for one or more electrodes of the plurality of electrodes 116 and 118 (e.g., including for each electrode of electrodes 116 and 118). One example way in which to generate the respective average level values is based on an RMS calculation. As described above, $A_i(t)$ represents a first time-varying measurement between two electrodes that horizontally neighbor each electrode and a horizontal distance between the two horizontally neighboring electrodes, and $Z_i(t)$ represents a second time-varying measurement between two electrodes that vertically neighbor each electrode and a vertical distance between the two vertically neighboring electrodes. $A_i(t)$ may be considered as a horizontal component (e.g., angular for ring electrodes and across for paddle electrodes), and $Z_i(t)$ may be considered as a longitudinal component.

The RMS value of the CSD for an electrode may be equal to $$CSD_i^{RMS} = \sigma \sqrt{\frac{1}{N} \sum_{j=1}^{N} |A_i(j) + Z_i(j)|^2}.$$

In the above equation, i is the electrode of interest, and N is the number of data points in a temporal window of CSD values that are determined. In this way, IMD 106 may aggregate the time-varying measurements of CSDs for each electrode into a single value for a that electrode. Instead of or in addition to using the voltage amplitude, the power or energy may be utilized. IMD 106 may use the RMS CSD value for purposes of comparison or ranking to determine which electrodes 116 and 118 are proximate to the oscillatory signal source. In some examples, the RMS CSD value may be associated with a color to provide a visual indication of the RMS.

In some examples, weighting may be applied to scale the $A_i(j)$ and $Z_i(j)$ samples. For example, more recently acquired $A_i(j)$ and $Z_i(j)$ samples may be weighted more heavily as compared to $A_i(j)$ and $Z_i(j)$ samples acquired less recently. As another example, $A_i(j)$ and $Z_i(j)$ samples that occurred closer in time to an event of interest may be weighted more heavily as compared to $A_i(j)$ and $Z_i(j)$ samples that occurred further away in time from the event of interest.

However, the RMS CSD values (or more generally, the aggregated time-varying measurements of the CSDs) may only provide information of relative amplitudes of the time-varying measurements of the CSDs. Phase information, which might be useful for discriminating between different physiologically relevant sources, may be lost. To address this, IMD 106 may be configured to determine a phase-magnitude (PHM) representation of the time-varying measurements of the CSDs.

The following describes an example algorithm for determining the PHM representation. IMD 106 may be configured to determine which electrode of electrodes 116 and 118 has the largest average level value (e.g., RMS CSD value). For the determined electrode, IMD 106 may perform a Fourier transform on its time-varying measurement and determine the largest frequency component of the time-varying measurement of the CSD. For instance, IMD 106 may determine that a particular frequency component for the time-varying measurement of the CSD has the largest Fourier transform coefficient (FTC). The particular frequency component is referred to as w0.

For one or more of electrodes 116 and 118, IMD 106 may determine the FTC at frequency w0. For example, assume that $A_{j,k}$ is the FTC at frequency wj for electrode k. In this example, $A_{w0,i}$ (e.g., the FTC for frequency w0 for the ith electrode) is equal to $M_i e^{j\phi_i}$. In this example, $M_i$ is the magnitude of frequency component with frequency w0, $\phi_i$ is the phase of the frequency component with frequency w0, and j is the square-root of −1. The values of $M_i$ and $\phi_i$ may be determined from an output of a fast Fourier transform (FFT) for a particular frequency component (e.g., w0). Other example ways in which to determine the values of $M_i$ and $\phi_i$ include Laplace transform, Hilbert transform, or real-time phase and amplitude tracking. The value of $A_{w0,i}$ is an example of the phase-magnitude representation. In some examples, the phase-magnitude representation may be further normalized.

For example, IMD 106 may determine for which electrode the FTC at frequency w0 is the largest. For instance, assume that there are six electrodes, and therefore, there are six values of $A_{w0}$ (i.e., $A_{w0,1}, A_{w0,2}, A_{w0,3}, A_{w0,4}, A_{w0,5}$, and $A_{w0,6}$). IMD 106 may determine which of these six values is the largest. Assume that FTC for the $k^{th}$ electrode for the frequency component with frequency w0 is the largest, where k is equal to 1-6 in the example where there are six electrodes. Accordingly, $A_{w0,k}$ equals $M_k e^{j\phi_k}$. In this example, $\phi_k$ is the phase of the frequency component with frequency w0 for the largest FTC of the time-varying CSD values at one or more of the electrodes 116 and 118. As noted above, frequency w0 is the largest frequency component of the time-varying CSD values that resulted in the greatest aggregated CSD value (e.g., greatest RMS value).

IMD 106 may subtract all FTC (e.g., $A_{w0,i}$) phase values from $\phi_k$ to get the phase normalized FTCs. For example, IMD 106 may determine $A_{w0,i\_norm}$ equals $M_i e^{j(\phi_i - \phi_k)}$. Normalization may not be necessary in all examples, or other types of normalization may be performed. In general, in the time-varying CSD signals there may not be reference phase that can be identified as 0-degree. Accordingly, a particular phase is selected to be the reference phase. In the above example, $\phi_k$ is the reference phase to which all of the other phases (e.g., $\phi_i$) are normalized. It may be possible to normalize the phase in some other manner.

In some examples, $A_{w0,i\_norm}$ and $(\phi_i - \phi_k)$ may be indicative of contributions of tissue surrounding each of the "i" electrodes as being signal sources or signal sinks. For example, from above, for each of electrode there is a normalized phase value (e.g., $\phi_i - \phi_k$), the differences between the normalized phase values may be indicative of which electrodes are separated by 180-degrees. For example, if the normalized phase value for a first electrode is 20-degrees and for a second electrodes is −160-degrees, then there is 180-degree difference between the first and second electrode. In this example, the first and second electrodes may be proximate to respective tissue that are acting as signal source and signal sink.

In this manner, $A_{w0,i\_norm}$ and $(\phi_i - \phi_k)$ may be utilized to determine which ones of electrodes 116 and 118 are most proximate to the oscillatory signal source, and similarly which ones are not proximate to the oscillatory signal source (e.g., normalized phase difference is not big). $A_{w0,i\_norm}$ and $(\phi_i - \phi_k)$ may together form the normalized phase-magnitude representation of time-varying measurements of the CSDs. $A_{w0,i\_norm}$ is referred to as normalized magnitude and $(\phi_i - \phi_k)$ is referred to as normalized phase. The normalized phase will be within the range of 0 to $2\pi$, and the values may be indicative of whether the oscillatory signal source is a current sink or a current source.

As above, phase information (e.g., normalized phase) may be useful because the phase information differentiates between tissue regions acting as oscillatory signal sources (e.g., outputting current) or as sinks (e.g., receiving current). It may be difficult to determine which one is a definitive source or sink without including DC components. However, when one region is out of phase with the other, they are functioning as different parts of the circuit (e.g., one is source and one is sink), such as receiving synaptic input versus generating output or generating a local inhibitory response. With the example techniques, it may be possible to differentiate the electrodes closest to the each (e.g., closest to source and sink without knowing whether a source or sink). By comparison, relying simply on the average level values (e.g., RMS) would just show a strong value for each region making them look more similar (e.g., not indicate that the tissue regions are acting as signal source and signal sink, but rather that oscillation is occurring proximately).

In some examples, programmer 104, based on instructions from IMD 106 or based on determination of circuitry of programmer 104, may be configured to provide a visual indication of the phase-magnitude representation. For ease, the following describes programmer 104 performing the operation, but in some examples, IMD 106 may perform the operations and output information to programmer 104 indicative of the results of the operation.

Figure 12:
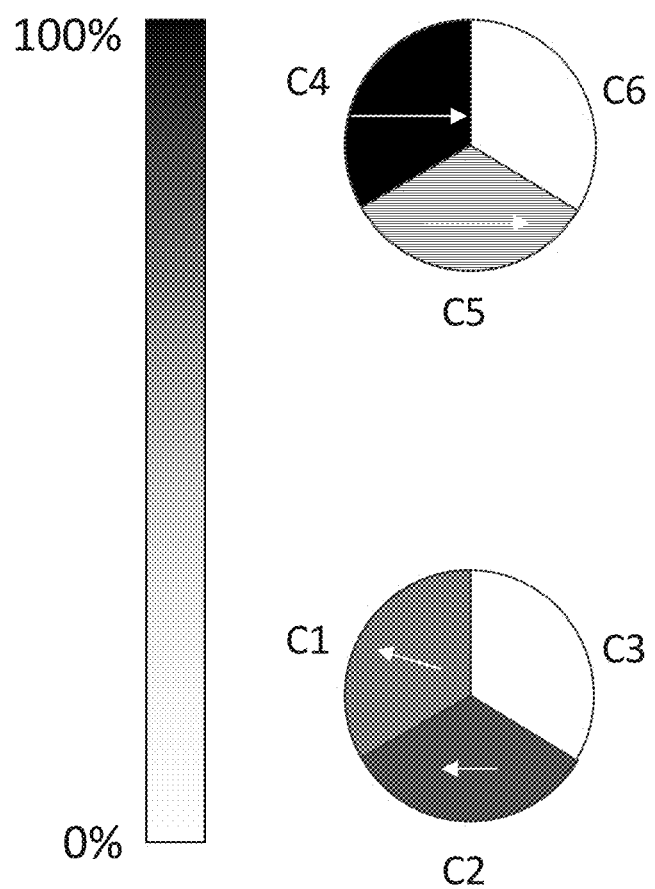
FIG. 12 is a conceptual diagram illustrating example phase-magnitude representation for CSDs for a plurality of electrodes.

For example, programmer 104 may utilize a circular color map divided into 256 levels such that normalized phase values close to 0 to $9\pi$ show up as red (at the two ends of the colorbar) while those close to $\pi$ show up as cyan (in the middle of the colorbar). In this way, a contrast in color is established based on the FTC phase differences (e.g., normalized phase values) between each electrode and the electrode with the largest FTC magnitude at the frequency component having frequency of w0. The utility of this representation is to distinguish physiological sinks and sources from each other using the time-varying measurements of the CSDs based on the phase information. Example of such display is illustrated in FIG. 12 using black-and-white gray-scale rather than color.

For the normalized magnitude, programmer 104 may be configured to map the absolute value of the normalized magnitude to the opacity of the corresponding color of normalized phase values. For instance, programmer 104 may determine the opacity of the color determined for $(\phi_i - \phi_k)$ based on the value of the absolute value of $A_{w0,1\_norm}$. In some examples, programmer 104 may assign 100% opacity to the maximum value of the normalized phase values, and assign 0% opacity (e.g., 100% transparency) to the minimum value of the normalized phase values.

The above describes an example way in which to display the phase-magnitude representation of the time-varying measurements of the CSD values. However, the example techniques are not so limited to the above ways in which to display the phase-magnitude representation. In general, the phase-magnitude representation for an electrode of electrodes 116 and 118 may be indicative of the magnitude and phase of a particular frequency component of the time-varying measurement of the CSD for that electrode. The particular frequency component may be a frequency component having the largest transform coefficient within a spectral band of interest in a time-varying measurement of a CSD having a largest average level value. For instance, the particular frequency component is the frequency component having a frequency of w0.

In this way, IMD 106 may configured to determine, for one or more electrodes of the plurality of electrodes 116 and 118, respective time-varying measurements of current source densities (CSDs). IMD 106 may aggregate, for one or more electrodes of the plurality of electrodes 116 and 118, the respective time-varying measurements of the CSDs to generate respective average level values for one or more electrodes of the plurality of electrodes (e.g., generate respective RMS values from the CDS values). IMD 106 may determine, for one or more electrodes of the plurality of electrodes 116 and 118, respective phase-magnitude representations of the time-varying measurements of the CSDs. The respective phase-magnitude representations are indicative of respective magnitudes and phases of a particular frequency component of respective time-varying measurements of the CSDs (e.g., the normalized magnitude ($A_{w0,i\_norm}$) and the normalized phase value ($\phi_i - \phi_k$) but normalization is not necessary in all examples). The particular frequency component is a frequency component having a largest transform coefficient within a spectral band of interest in a time-varying measurement of a CSD having a largest average level value (e.g., the frequency component is the frequency w0).

IMD 106 may generate information indicative of the respective average level values and respective phase-magnitude representations. For example, IMD 106 may output information indicative of the average level values and the phase-magnitude representations, and programmer 104 may provide a visual representation that a clinician can use to determine which electrodes 116 and 118 are proximate to the oscillatory signal source, and possibly whether the oscillatory signal source is a current sink or a current source. In some examples, instead of or in addition to using visual representations, IMD 106 may utilize the average level values and the phase-magnitude representations to determine which electrodes are most proximate (e.g., closest to) to an oscillatory signal source and/or which electrodes are most distal (e.g., farthest away from). IMD 106 may generate information indicative of the determined electrodes that are most proximate to the oscillatory signal source.

The above example techniques are described with respect to DBS. However, the example techniques are not so limited. For instance, the example techniques may be used with evoked responses. For example, a stimulation pulse or burst from an electrode on the same or another lead evokes a neural response and the CSD is used, in accordance with one or more examples described in this disclosure, to identify which electrodes are closest or furthest from the tissue with the neural response. The example techniques may be used with DBS, spinal stimulation, and peripheral nerve stimulation scenarios, as a few examples.

Figure 2:
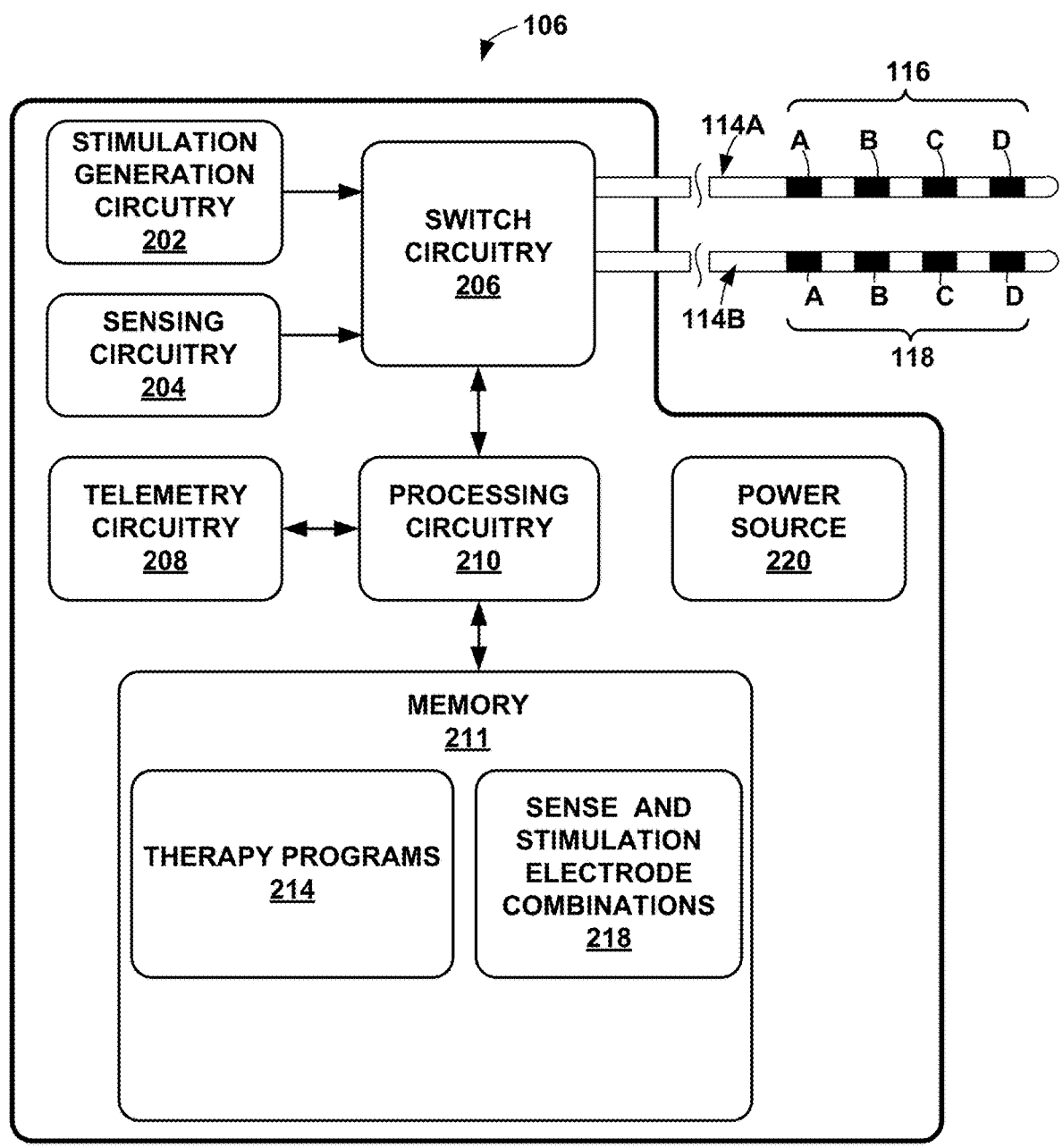
FIG. 2 is a block diagram of the example IMD of FIG. 1 for delivering adaptive DBS therapy according to an example of the techniques of the disclosure.

FIG. 2 is a block diagram of the example IMD 106 of FIG. 1 for delivering adaptive deep brain stimulation therapy. In the example shown in FIG. 2, IMD 106 includes processing circuitry 210, memory 211, stimulation generation circuitry 202, sensing circuitry 204, switch circuitry 206, telemetry circuitry 208, and power source 220. Each of these circuits may be or include electrical circuitry configured to perform the functions attributed to each respective circuit. Memory 211 may include any volatile or non-volatile media, such as a random-access memory (RAM), read only memory (ROM), non-volatile RAM (NVRAM), electrically erasable programmable ROM (EEPROM), flash memory, and the like. Memory 211 may store computer-readable instructions that, when executed by processing circuitry 210, cause IMD 106 to perform various functions. Memory 211 may be a storage device or other non-transitory medium.

In the example shown in FIG. 2, memory 211 stores therapy programs 214 and sense electrode combinations and associated stimulation electrode combinations 218, in separate memories within memory 211 or separate areas within memory 211. Each stored therapy program 214 defines a particular set of electrical stimulation parameters (e.g., a therapy parameter set), such as a stimulation electrode combination, electrode polarity, current or voltage amplitude, pulse width, and pulse rate. In some examples, individual therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

Sense and stimulation electrode combinations 218 stores sense electrode combinations and associated stimulation electrode combinations. As described above, in some examples, sense and stimulation electrode combinations 218 may include the same subset of electrodes 116, 118, a housing of IMD 106 functioning as an electrode, or may include different subsets or combinations of such electrodes. Thus, memory 211 can store a plurality of sense electrode combinations and, for each sense electrode combination, store information identifying the stimulation electrode combination that is associated with the respective sense electrode combination. The associations between sense and stimulation electrode combinations can be determined, e.g., by a clinician or automatically by processing circuitry 210. In some examples, corresponding sense and stimulation electrode combinations may comprise some or all of the same electrodes. In other examples, however, some or all of the electrodes in corresponding sense and stimulation electrode combinations may be different. For example, a stimulation electrode combination may include more electrodes than the corresponding sense electrode combination in order to increase the efficacy of the stimulation therapy.

Stimulation generation circuitry 202, under the control of processing circuitry 210, generates stimulation signals for delivery to patient 112 via selected combinations of electrodes 116, 118. An example range of electrical stimulation parameters believed to be effective in DB S to manage a movement disorder of patient include:

1. Pulse Rate, i.e., Frequency: between approximately 40 Hertz and approximately 500 Hertz, such as between approximately 90 to 170 Hertz or such as approximately 90 Hertz.
2. In the case of a voltage controlled system, Voltage Amplitude: between approximately 0.1 volts and approximately 50 volts, such as between approximately 2 volts and approximately 3 volts.
3. In the case of a current controlled system, Current Amplitude: between approximately 1 milliamps to approximately 3.5 milliamps, such as between approximately 1.0 milliamps and approximately 1.75 milliamps.

4. Pulse Width: between approximately 50 microseconds and approximately 500 microseconds, such as between approximately 50 microseconds and approximately 200 microseconds.

Accordingly, in some examples, stimulation generation circuitry 202 generates electrical stimulation signals in accordance with the electrical stimulation parameters noted above. Other ranges of therapy parameter values may also be useful, and may depend on the target stimulation site within patient 112. While stimulation pulses are described, stimulation signals may be of any form, such as continuous-time signals (e.g., sine waves) or the like.

Processing circuitry 210 may include fixed function processing circuitry and/or programmable processing circuitry, and may comprise, for example, any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 210 herein may be embodied as firmware, hardware, software or any combination thereof. Processing circuitry 210 may control stimulation generation circuitry 202 according to therapy programs 214 stored in memory 211 to apply particular stimulation parameter values specified by one or more of programs, such as voltage amplitude or current amplitude, pulse width, and/or pulse rate.

In the example shown in FIG. 2, the set of electrodes 116 includes electrodes 116A, 116B, 116C, and 116D, and the set of electrodes 118 includes electrodes 118A, 118B, 118C, and 118D. Processing circuitry 210 also controls switch circuitry 206 to apply the stimulation signals generated by stimulation generation circuitry 202 to selected combinations of electrodes 116, 118. In particular, switch circuitry 204 may couple stimulation signals to selected conductors within leads 114, which, in turn, deliver the stimulation signals across selected electrodes 116, 118. Switch circuitry 206 may be a switch array, switch matrix, multiplexer, or any other type of switching module configured to selectively couple stimulation energy to selected electrodes 116, 118 and to selectively sense neurological brain signals with selected electrodes 116, 118. Hence, stimulation generation circuitry 202 is coupled to electrodes 116, 118 via switch circuitry 206 and conductors within leads 114. In some examples, however, IMD 106 does not include switch circuitry 206.

Stimulation generation circuitry 202 may be a single channel or multi-channel stimulation generator. In particular, stimulation generation circuitry 202 may be capable of delivering a single stimulation pulse, multiple stimulation pulses, or a continuous signal at a given time via a single electrode combination or multiple stimulation pulses at a given time via multiple electrode combinations. In some examples, however, stimulation generation circuitry 202 and switch circuitry 206 may be configured to deliver multiple channels on a time-interleaved basis. For example, switch circuitry 206 may serve to time divide the output of stimulation generation circuitry 202 across different electrode combinations at different times to deliver multiple programs or channels of stimulation energy to patient 112. Alternatively, stimulation generation circuitry 202 may comprise multiple voltage or current sources and sinks that are coupled to respective electrodes to drive the electrodes as cathodes or anodes. In this example, IMD 106 may not require the functionality of switch circuitry 206 for time-interleaved multiplexing of stimulation via different electrodes.

Electrodes 116, 118 on respective leads 114 may be constructed of a variety of different designs. For example, one or both of leads 114 may include two or more electrodes at each longitudinal location along the length of the lead, such as multiple electrodes, e.g., arranged as segments, at different perimeter locations around the perimeter of the lead at each of the locations A, B, C, and D.

As an example, one or both of leads 114 may include radially-segmented DBS arrays (rDBSA) of electrodes. In the rDBSA, as one example, there may be a first ring electrode of electrodes 116 around the perimeter of lead 114A at a first longitudinal location on lead 114A (e.g., location A). Below the first ring electrode, there may be three segmented electrodes of electrodes 116 around the perimeter of lead 114A at a second longitudinal location on lead 114A (e.g., location B). Below the three segmented electrodes, there may be another set of three segmented electrodes of electrodes 116 around the perimeter of lead 114A at a third longitudinal location of lead 114A (e.g., location C). Below the three segmented electrodes, there may be a second ring electrode of electrodes 116 around the perimeter of lead 114A (e.g., location D). Electrodes 118 may be similarly positioned along lead 114B.

The above is one example of the rDBSA array of electrodes, and the example techniques should not be considered limited to such an example. There may be other configurations of electrodes for DBS. Moreover, the example techniques are not limited to DBS, and other electrode configurations are possible.

In one example, the electrodes 116, 118 may be electrically coupled to switch circuitry 206 via respective wires that are straight or coiled within the housing of the lead and run to a connector at the proximate end of the lead. In another example, each of the electrodes 116, 118 of the leads 114 may be electrodes deposited on a thin film. The thin film may include an electrically conductive trace for each electrode that runs the length of the thin film to a proximate end connector. The thin film may then be wrapped (e.g., a helical wrap) around an internal member to form the leads 114. These and other constructions may be used to create a lead with a complex electrode geometry.

Although sensing circuitry 204 is incorporated into a common housing with stimulation generation circuitry 202 and processing circuitry 210 in FIG. 2, in other examples, sensing circuitry 204 may be in a separate housing from IMD 106 and may communicate with processing circuitry 210 via wired or wireless communication techniques. Example neurological brain signals include, but are not limited to, a signal generated from local field potentials (LFPs) within one or more regions of brain 120. EEG and ECoG signals are examples of local field potentials that may be measured within brain 120. LFPs, EEG and ECoG may be different measurements of the same bioelectric signals in the brain. The neurons generate the signals, and if measured at depth, it is LFP, if measured on the coretex, it is ECoG, if on the scalp, it is EEG. In general, the bioelectric signals may be formed by one or more oscillatory signal sources. The set of electrodes 116 and 118 that are most proximate to the oscillatory signal sources are good candidates to use for delivering therapy.

Telemetry circuitry 208 supports wireless communication between IMD 106 and an external programmer 104 or another computing device under the control of processing circuitry 210. Processing circuitry 210 of IMD 106 may receive, as updates to programs, values for various stimulation parameters such as magnitude and electrode combination, from programmer 104 via telemetry circuitry 208.

The updates to the therapy programs may be stored within therapy programs 214 portion of memory 211. Telemetry circuitry 208 in IMD 106, as well as telemetry modules in other devices and systems described herein, such as programmer 104, may accomplish communication by radiofrequency (RF) communication techniques. In addition, telemetry circuitry 208 may communicate with external medical device programmer 104 via proximate inductive interaction of IMD 106 with programmer 104. Accordingly, telemetry circuitry 208 may send information to external programmer 104 on a continuous basis, at periodic intervals, or upon request from IMD 106 or programmer 104.

Power source 220 delivers operating power to various components of IMD 106. Power source 220 may include a small rechargeable or non-rechargeable battery and a power generation circuit to produce the operating power. Recharging may be accomplished through proximate inductive interaction between an external charger and an inductive charging coil within IMD 104. In some examples, power requirements may be small enough to allow IMD 104 to utilize patient motion and implement a kinetic energy-scavenging device to trickle charge a rechargeable battery. In other examples, traditional batteries may be used for a limited period of time.

In one example, processing circuitry 210 of IMD 106 senses, via electrodes 116, 118 interposed along leads 114 (and sensing circuitry 204), one or more bioelectric signals of brain 120 of patient 112. Further, processing circuitry 210 of IMD 106 delivers, via electrodes 116, 118 (and stimulation generation circuitry 202), electrical stimulation therapy to patient 112 based on the sensed one or more bioelectric signals of brain 120. The adaptive DBS therapy is defined by one or more therapy programs 214 having one or more parameters stored within memory 211. For example, the one or more parameters include a current amplitude (for a current-controlled system) or a voltage amplitude (for a voltage-controlled system), a pulse rate or frequency, and a pulse width, or a number of pulses per cycle. In examples where the electrical stimulation is delivered according to a "burst" of pulses, or a series of electrical pulses defined by an "on-time" and an "off-time," the one or more parameters may further define one or more of a number of pulses per burst, an on-time, and an off-time. Processing circuitry 210, via electrodes 116, 118, delivers to patient 112 adaptive DBS and may adjust one or more parameters defining the electrical stimulation based on corresponding parameters of the sensed one or more bioelectric signals of brain 120.

In some examples, processing circuitry 210 continuously measures the one or more bioelectric signals in real time. In other examples, processing circuitry 210 periodically samples the one or more bioelectric signals according to a predetermined frequency or after a predetermined amount of time. In some examples, processing circuitry 210 periodically samples the signal at a frequency of approximately 150, 250, 500, or 1000 Hertz.

According to the techniques of the disclosure, processing circuitry 210 may be configured to determine which electrodes 116, 118 should be used to deliver electrical stimulation. To determine which electrodes 116, 118 to use for delivering electrical stimulation, processing circuitry 210 may determine which electrodes 116, 118 have the greatest current source density (CSD) value due to sensing of time-varying signal from the oscillatory signal source. However, other techniques to determine which electrodes 116, 118 to use to deliver electrical stimulation are possible.

As one example way to determine the CSD value, processing circuitry 210 may cause sensing circuitry 204 to measure the voltage across pairs of electrodes 116, 118, where the voltage across the pairs of electrodes 116, 118 is due to the time-varying signal generated by the oscillatory signal source. The result of the measured voltages may be a set of differential voltages. Processing circuitry 210 may then determine the difference between differential voltages of the set of differential voltages to determine a CSD value for one or more of electrodes 116, 118 (expect for possibly the top and bottom electrodes).

For example, processing circuitry 210 may determine, for one or more electrodes of the plurality of electrodes 116 and 118, respective time-varying measurements of CSDs. As one example, processing circuitry 210 may determine, for one or more electrodes of the plurality of electrodes, respective first time-varying measurements based on second-order voltage differences between two electrodes that horizontally neighbor each electrode and a horizontal distance between the two horizontally neighboring electrodes and determine, for one or more electrodes of the plurality of electrodes, respective second time-varying measurements based on second-order voltage differences between two electrodes that vertically neighbor each electrode and a vertical distance between the two vertically neighboring electrodes. Processing circuitry 210 may determine respective time-varying measurements of the CSDs based on the respective first time-varying measurements and the second time-varying measurements.

As one example, processing circuitry 210 may scale the respective first-time varying measurements based on a radius of leads 104A, B that includes the respective electrodes of electrodes 116, 118 (e.g., determine Mt) as described above by scaling by a factor of 1/r). Also, in some examples, processing circuitry 210 may scale at least one of the respective first time-varying measurements or the second time-varying measurements based on an anisotropy of local tissue impedance of the two horizontally neighboring electrodes or the two vertically neighboring electrodes. For instance, processing circuitry 210 may multiply the first and second time-varying measurements by of the CSDs by σ.

Processing circuitry 210 may be configured to aggregate, for one or more electrodes of the plurality of electrodes 116, 118, the respective time-varying measurements of the CSDs to generate respective average level values for one or more electrodes of the plurality of electrodes. For example, processing circuitry 210 may be configured to determine, for one or more electrodes of the plurality of electrodes 116, 118, respective root-mean-square (RMS) values based on the respective first time-varying measurement and the second time-varying measurement. As described above, processing circuitry 210 may perform the operations of the following equation to generate the average level value as a way to aggregate the respective time-varying measurements of the CSDs $$CSD_i^{RMS} = \sigma \sqrt{\frac{1}{N} \sum_{j=1}^{N} |A_i(j) + Z_i(j)|^2},$$

where i is the electrode of interest, and N is the number of data points in a temporal window of CSD values that are determined. Techniques other than techniques to calculate RMS values may be used to aggregate time-varying measurements of the CSD values.

In addition to generating the average level values, processing circuitry 210 may determine for one or more electrodes of the plurality of electrodes 116, 118, respective phase-magnitude representations of the time-varying measurements of the CSDs. The respective phase-magnitude representations are indicative of respective magnitudes and phases of a particular frequency component of respective time-varying measurements of the CSDs, where the particular frequency component is a frequency component having a largest transform coefficient in a time-varying measurement of a CSD having a largest average level value. There may be various ways in which to determine the phase-magnitude representation.

For example, processing circuitry 210 may determine which electrode of electrodes 116, 118 has a highest average level value and determine a largest frequency component in the time-varying measurement of the CSD for the electrode having the highest average level value. For example, assume that electrode X has the highest average level value of the time-varying measurements of the CSDs, and assume that frequency w0 is the largest frequency component in the time-varying measurement CSD at electrode X.

Processing circuitry 210 may determine, for one or more electrodes of the plurality of electrodes 116, 118, respective transform coefficients (e.g., Fourier transform coefficients (FTCs)) at the determined largest frequency component (e.g., w0) in respective time-varying measurements of the CSDs. Processing circuitry 210 may also determine, for one or more electrodes of the plurality of electrodes 116, 118, respective phase values associated with the respective transform coefficients. For example, assume that $A_{w0,i}$ is the FTC for frequency w0 for the ith electrode, and is equal to $M_i e^{j\phi_i}$. In this example, $M_i$ is the magnitude of frequency component with frequency w0, $\phi_i$ is the phase of the frequency component with frequency w0 (e.g., phase value associated with transform coefficient), and j is the square-root of −1.

In this example, processing circuitry 210 may determine respective phase-magnitude representations based on the determined respective transform coefficients and the respective phase values. For example, processing circuitry 210 may utilize the $M_i$ and $\phi_i$ values to determine respective phase-magnitude representations for electrode i. As one example, processing circuitry 210 may determine a largest transform coefficient from the respective transform coefficients. For instance, $A_{w0,k}$ represents the largest transform coefficient and is the coefficient of electrode-k. $A_{w0,k}$ equals $M_k e^{j\phi_k}$. Processing circuitry 210 may determine a phase value associated with the determined largest transform coefficient (e.g., determine $\phi_k$). Processing circuitry 210 may determine a difference between respective phase values associated with respective transform coefficients and the determined phase value associated with the determined largest transform coefficient (e.g., determine ($\phi_i - \phi_k$)). Processing circuitry 210 may determine respective phase-magnitude representations based on the determined difference and the determined respective transform coefficients (e.g., $A_{w0,i\_norm}$ equals $M_i e^{j(\phi_i - \phi_k)}$).

In some examples, processing circuitry 210 may be configured to generate information indicative of the respective average level values and respective phase-magnitude representations. As one example, processing circuitry 210 may output color information that represents the different average level values for the electrodes and output color information for the phase and the opacity of the color for the phase is based on the magnitude. As another example, processing circuitry 210 may output average level values and phase-magnitude representations as data values.

In some examples, processing circuitry 210 may be configured to determine which electrodes of the one or more electrodes 116, 118 are most proximate (e.g., closest to) or distal (e.g., farthest from) to an oscillatory signal source (e.g., source or sink) based on the generated information indicative of the respective average level values and the respective phase-magnitude representations utilizing the above example techniques. In such examples, processing circuitry 210 may generate and output information indicative of the determined electrodes.

Processing circuitry 210 may select the determined electrodes that are most proximate to the signal source for delivering the electrical stimulation. Processing circuitry 210 may cause stimulation generation circuitry 202 and/or switch circuitry 206 to deliver the electrical stimulation with the selected electrodes, so as to deliver the stimulation from electrodes determined to be most proximate to the oscillatory source.

Figure 3:
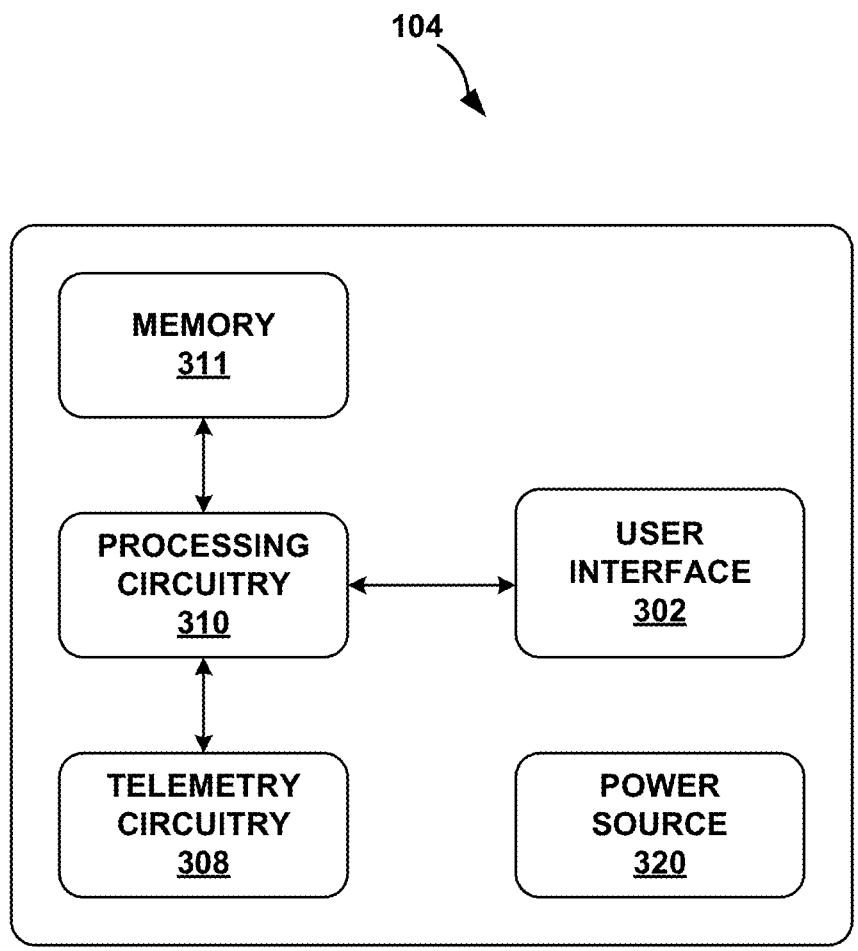
FIG. 3 is a block diagram of the external programmer of FIG. 1 for controlling delivery of adaptive DBS therapy according to an example of the techniques of the disclosure.

FIG. 3 is a block diagram of the external programmer 104 of FIG. 1. Although programmer 104 may generally be described as a hand-held device, programmer 104 may be a larger portable device or a more stationary device. In addition, in other examples, programmer 104 may be included as part of an external charging device or include the functionality of an external charging device. As illustrated in FIG. 3, programmer 104 may include processing circuitry 310, memory 311, user interface 302, telemetry circuitry 308, and power source 320. Memory 311 may store instructions that, when executed by processing circuitry 310, cause processing circuitry 310 and external programmer 104 to provide the functionality ascribed to external programmer 104 throughout this disclosure. Each of these components, or modules, may include electrical circuitry that is configured to perform some or all of the functionality described herein. For example, processing circuitry 310 may include processing circuitry configured to perform the processes discussed with respect to processing circuitry 310.

In general, programmer 104 comprises any suitable arrangement of hardware, alone or in combination with software and/or firmware, to perform the techniques attributed to programmer 104, and processing circuitry 310, user interface 302, and telemetry circuitry 308 of programmer 104. In various examples, programmer 104 may include one or more processors, which may include fixed function processing circuitry and/or programmable processing circuitry, as formed by, for example, one or more microprocessors, DSPs, ASICs, FPGAs, or any other equivalent integrated or discrete logic circuitry, as well as any combinations of such components. Programmer 104 also, in various examples, may include a memory 311, such as RAM, ROM, PROM, EPROM, EEPROM, flash memory, a hard disk, a CD-ROM, comprising executable instructions for causing the one or more processors to perform the actions attributed to them. Moreover, although processing circuitry 310 and telemetry circuitry 308 are described as separate modules, in some examples, processing circuitry 310 and telemetry circuitry 308 may be functionally integrated with one another. In some examples, processing circuitry 310 and telemetry circuitry 308 correspond to individual hardware units, such as ASICs, DSPs, FPGAs, or other hardware units.

Memory 311 (e.g., a storage device) may store instructions that, when executed by processing circuitry 310, cause processing circuitry 310 and programmer 104 to provide the functionality ascribed to programmer 104 throughout this disclosure. For example, memory 311 may include instructions that cause processing circuitry 310 to obtain a parameter set from memory or receive a user input and send a corresponding command to IMD 106, or instructions for any other functionality. In addition, memory 311 may include a plurality of programs, where each program includes a parameter set that defines stimulation therapy.

User interface 302 may include a button or keypad, lights, a speaker for voice commands, a display, such as a liquid crystal (LCD), light-emitting diode (LED), or organic light-emitting diode (OLED). In some examples the display may be a touch screen. User interface 302 may be configured to display any information related to the delivery of stimulation therapy, identified patient behaviors, sensed patient parameter values, patient behavior criteria, or any other such information. User interface 302 may also receive user input via user interface 302. The input may be, for example, in the form of pressing a button on a keypad or selecting an icon from a touch screen.

Telemetry circuitry 308 may support wireless communication between IMD 106 and programmer 104 under the control of processing circuitry 310. Telemetry circuitry 308 may also be configured to communicate with another computing device via wireless communication techniques, or direct communication through a wired connection. In some examples, telemetry circuitry 308 provides wireless communication via an RF or proximal inductive medium. In some examples, telemetry circuitry 308 includes an antenna, which may take on a variety of forms, such as an internal or external antenna.

Examples of local wireless communication techniques that may be employed to facilitate communication between programmer 104 and IMD 106 include RF communication according to the 802.11 or Bluetooth specification sets or other standard or proprietary telemetry protocols. In this manner, other external devices may be capable of communicating with programmer 104 without needing to establish a secure wireless connection.

In some examples, processing circuitry 310 of external programmer 104 defines the parameters of electrical stimulation therapy, stored in memory 311, for delivering adaptive DBS to patient 112. In one example, processing circuitry 310 of external programmer 104, via telemetry circuitry 308, issues commands to IMD 106 causing IMD 106 to deliver electrical stimulation therapy via electrodes 116, 118 via leads 114.

In one or more examples, programmer 104 may be configured to perform one or more of the example techniques described in this disclosure. For instance, processing circuitry 310 may be configured to perform any of the example operations described above with respect to processing circuitry 210. For example, as described above, IMD 106 includes sensing circuitry 204 to receive the bioelectric signals from one or more electrodes, and stimulation generation circuitry 202 to deliver the electrical stimulation having the final therapy parameter value. In some examples, telemetry circuitry 308 may be configured to receive information of the bioelectric signals received by sensing circuitry 204 (e.g., telemetry circuitry 208 of IMD 106 may output information of the bioelectric signal to telemetry circuitry 308 of programmer 104). Processing circuitry 310 may perform the example operations described above with respect to processing circuitry 210. For example, processing circuitry 310 may determine which electrodes have a particular spatial relationship to the signal source (e.g., closest to the source) and may select these electrodes for delivering the electrical stimulation. Processing circuitry 310 may then issues commands to IMD 106 causing IMD 106 to deliver electrical stimulation therapy via the selected electrodes.

Figure 4A:
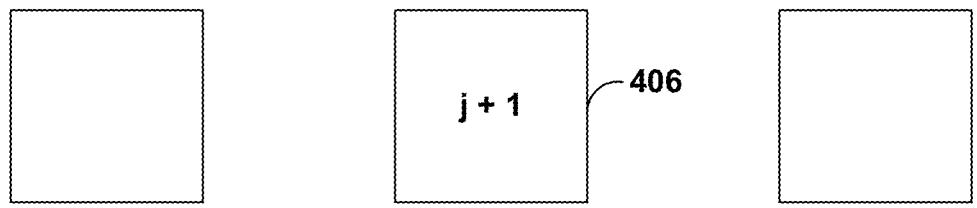
FIGS. 4A and 4B are conceptual diagrams illustrating examples of electrodes on a lead with which current source density (CSD) measurements are performed.
Figure 4A:
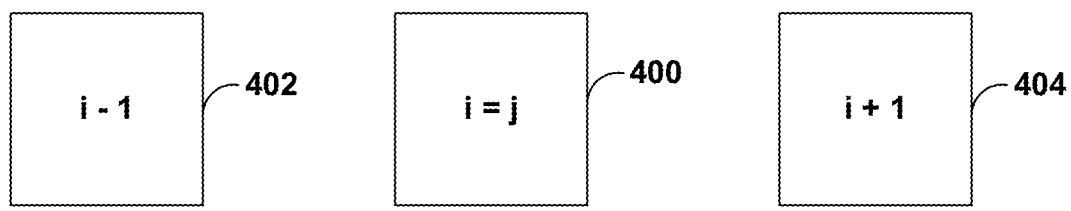
Figure 4A:
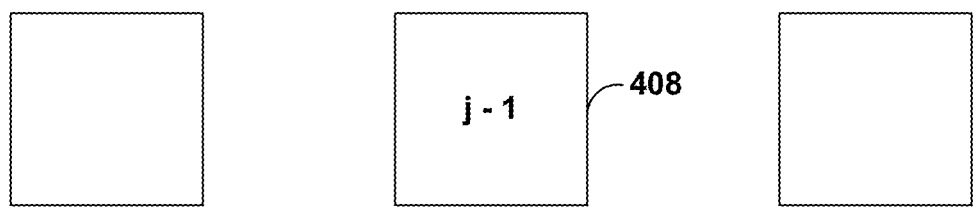
Figure 4B:
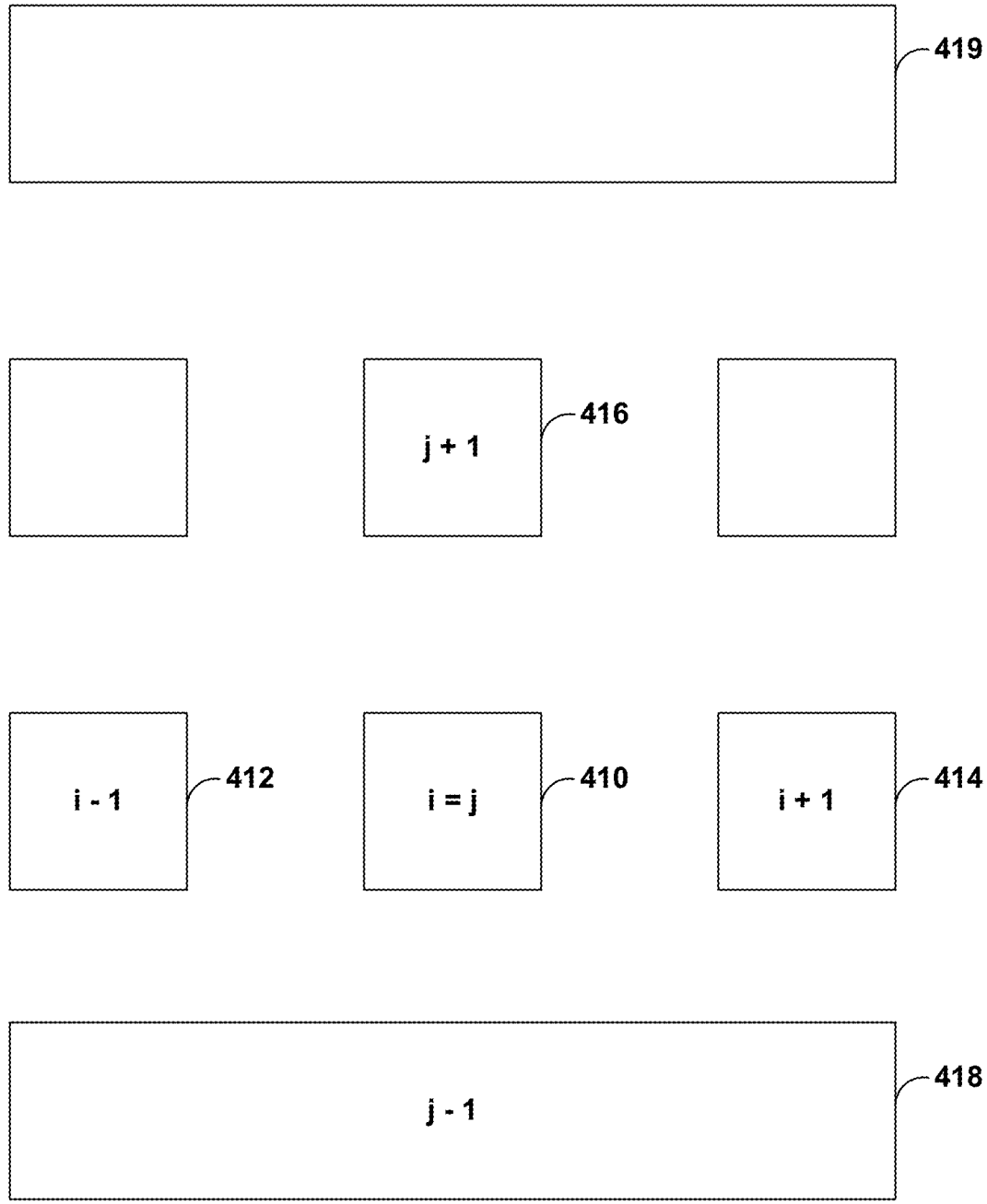

FIGS. 4A and 4B are conceptual diagrams illustrating examples of electrodes on a lead with which current source density (CSD) measurements are performed. FIG. 4A illustrates segment electrodes. To determine the CSD measurements for electrode 400, processing circuitry 210 or 310 may determine the difference between the voltage at electrode i 400 and electrode i+1 404, which is $\Delta V_{i,i+1}$ and determine the difference between the voltage at electrode i 400 and electrode i−1 402, which is $\Delta V_{i-1,i}$. For the first-time varying measurements, the processing circuitry 210 or 310 may then determine a difference between $\Delta V_{i-1,i}$ and $\Delta V_{i,i+1}$ as the second-order voltage differences between two electrodes that horizontally neighbor each electrode. Similarly, processing circuitry 210 or 310 may determine the difference between the voltage at electrode j 400 and electrode j+1 406, which is $\Delta V_{j,j+1}$ and determine the difference between the voltage at electrode j 400 and electrode j−1 408, which is $\Delta V_{j-1,j}$. The processing circuitry 210 or 310 may then determine a difference between $\Delta V_{j-1,j}$ and $\Delta V_{j,j+1}$ as the second-order voltage differences between two electrodes that vertically neighbor each electrode.

In some examples, the computation may be based on the "right hand rule" around the electrode (e.g., $\Delta V_{i-1,i}$=voltage at electrode 400−voltage at electrode 402 and $\Delta V_{i,i+1}$=voltage at electrode 404−voltage at electrode 400). Then, processing circuitry 210 may compute the approximation of the second-order difference $\Delta V_{i,i+1} - \Delta V_{i-1,i}$. The same applies in the z-direction (e.g., up and down).

In some examples, the most accurate estimate of the CSD may be achieved when the all voltages (or more typically, the voltage differences $\Delta V$), horizontal and vertical, are measured simultaneously. This is true for time domain or frequency domain (at least when subtracting phasors). Otherwise, measuring at separate times would require first aggregating (e.g. computing the power), then subtracting, which would only be a rough approximation of the CSD.

FIG. 4B is similar to FIG. 4A, except FIG. 4B includes ring electrodes 418 and 419. To determine the CSD measurements for electrode 410, processing circuitry 210 may determine the difference between the voltage at electrode i 410 and electrode i+1 414, which is $\Delta V_{i,i+1}$ and determine the difference between the voltage at electrode i 410 and electrode i−1 412, which is $\Delta V_{i-1,i}$. For the first-time varying measurements, the processing circuitry 210 or 310 may then determine a difference between $\Delta V_{i-1,i}$ and $\Delta V_{i,i+1}$ as the second-order voltage differences between two electrodes that horizontally neighbor each electrode. Similarly, processing circuitry 210 or 310 may determine the difference between the voltage at electrode j 410 and electrode j+1 416, which is $\Delta V_{j,j-1}$ and determine the difference between the voltage at electrode j 410 and electrode j−1 418, which is $\Delta V_{j-1,j}$. The processing circuitry 210 or 310 may then determine a difference between $\Delta V_{j-1,j}$ and $\Delta V_{j,j+1}$ as the second-order voltage differences between two electrodes that vertically neighbor each electrode.

In the example techniques described above, processing circuitry 210 or 310 may be configured to perform various operations as a way to determine CSD values. For instance, processing circuitry 210 or 310 may perform filtering or Fourier transforms as a way to perform operations in the time-domain or frequency-domain. FIGS. 5-8 are flowcharts that illustrate the example ways in which processing circuitry 210 or 310 may perform the example operations to determine the time-varying measurements of the CSD values. For ease of illustration, the examples are described with respect to processing circuitry 210 but may be performed by processing circuitry 310 or a combination of processing circuitry 210 and processing circuitry 310.

Figure 5:
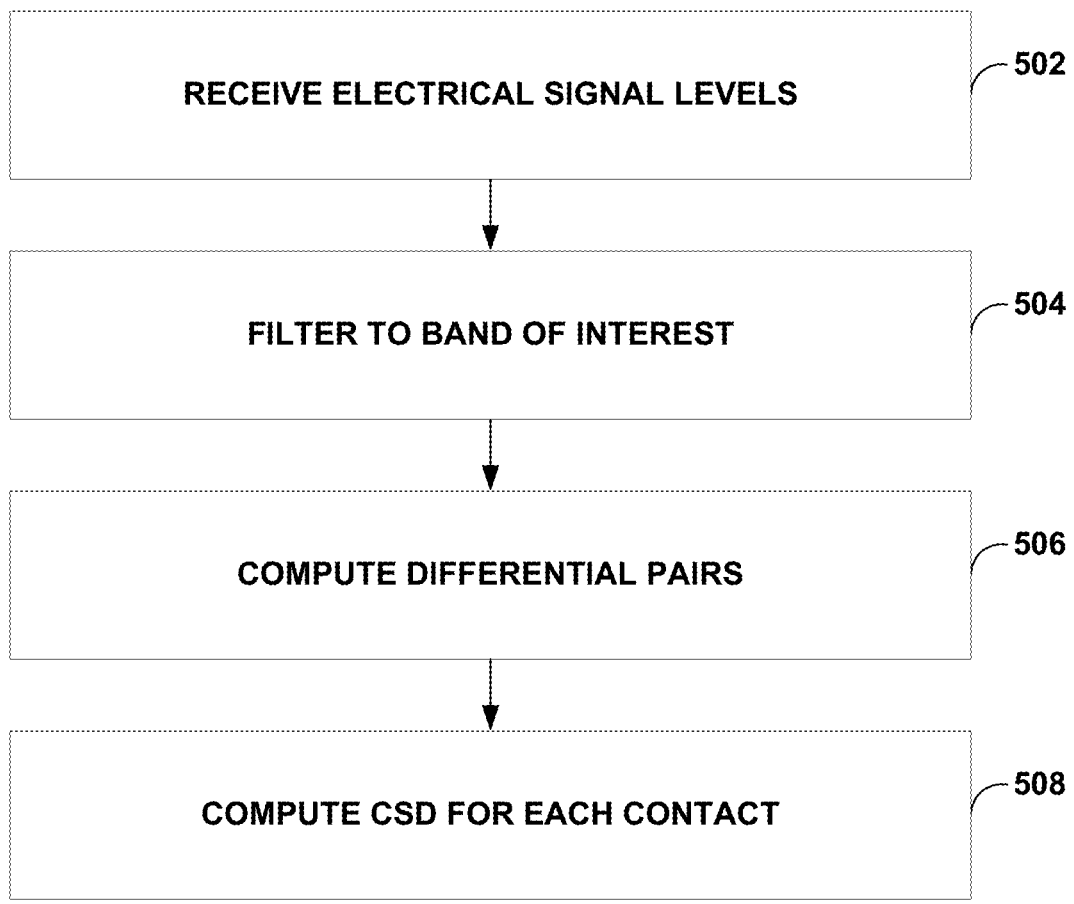
FIG. 5 is a flowchart illustrating an example operation in accordance with techniques of the disclosure.

FIG. 5 is a flowchart illustrating an example operation in accordance with techniques of the disclosure. In the example, processing circuitry 210 may receive information indicative of electrical signal levels (e.g., voltage measurements) from electrodes 116, 118 (502). For example, memory 211 may store the electrical signal levels and processing circuitry 210 may receive the electrical signal levels from memory 211. Processing circuitry 210 may filter (e.g., bandpass filter) the received electrical signal levels to a band of interest (e.g., to filter out all frequency components except the beta band) (504). Processing circuitry 210 may compute differential pairs based on the filtered electrical signal levels (e.g., $\Delta V_{i,i-1} - \Delta V_{i+1,i}$ and $\Delta V_{j,j-1} - \Delta V_{j+1,j}$) (506). Processing circuitry 210 may compute CSD values for each contact (e.g., electrode) based on the computed differential pairs (e.g., determine $A_i(t)$ and $Z_i(t)$ and add them together to determine the CSD values) (508).

Figure 6:
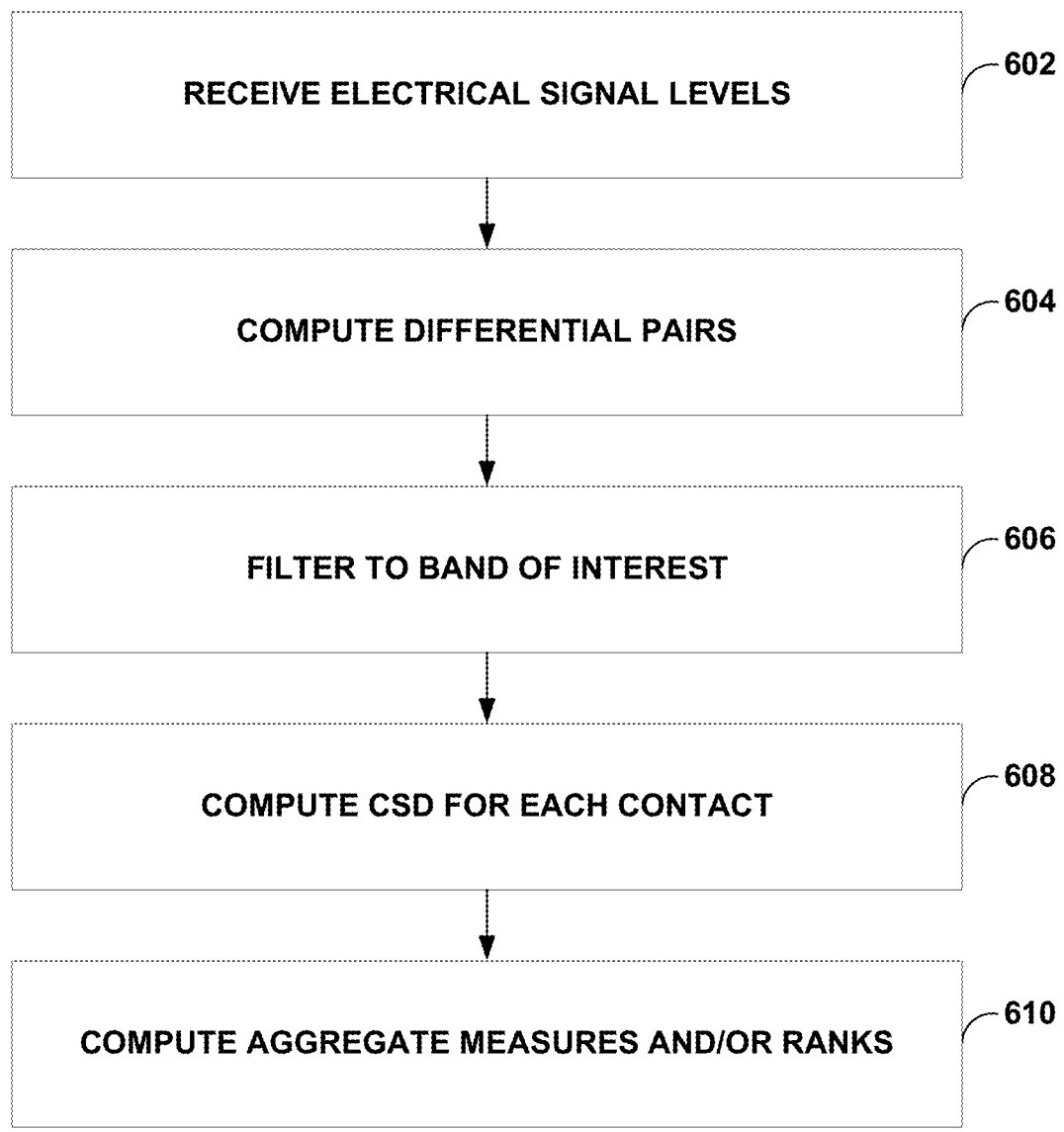
FIG. 6 is a flowchart illustrating another example operation in accordance with techniques of the disclosure.

FIG. 6 is a flowchart illustrating another example operation in accordance with techniques of the disclosure. In the example, processing circuitry 210 may receive electrical signal levels (e.g., voltage measurements) from electrodes 116, 118 (602). For example, memory 211 may store the electrical signal levels and processing circuitry 210 may receive the electrical signal levels from memory 211. Processing circuitry 210 may compute differential pairs based on the electrical signal levels (e.g., $\Delta V_{i,i-1} - \Delta V_{i+1,i}$ and $\Delta V_{j,j-1} - \Delta V_{j+1,j}$) (604). Processing circuitry 210 may filter (e.g., bandpass filter) the results of the computed differential pairs to a band of interest (e.g., to filter out all frequency components except the beta band) (606). Processing circuitry 210 may compute CSD values for each contact (e.g., electrode) based on the filtered computed differential pairs (e.g., determine $A_i(t)$ and $Z_i(t)$ and add them together to determine the CSD values) (608). Processing circuitry 210 may compute aggregate measures and/or ranks (610). An example of the aggregate measurement is the average level value (e.g., RMS value) and an example of the rank is the phase-magnitude representation, as described above.

Figure 7:
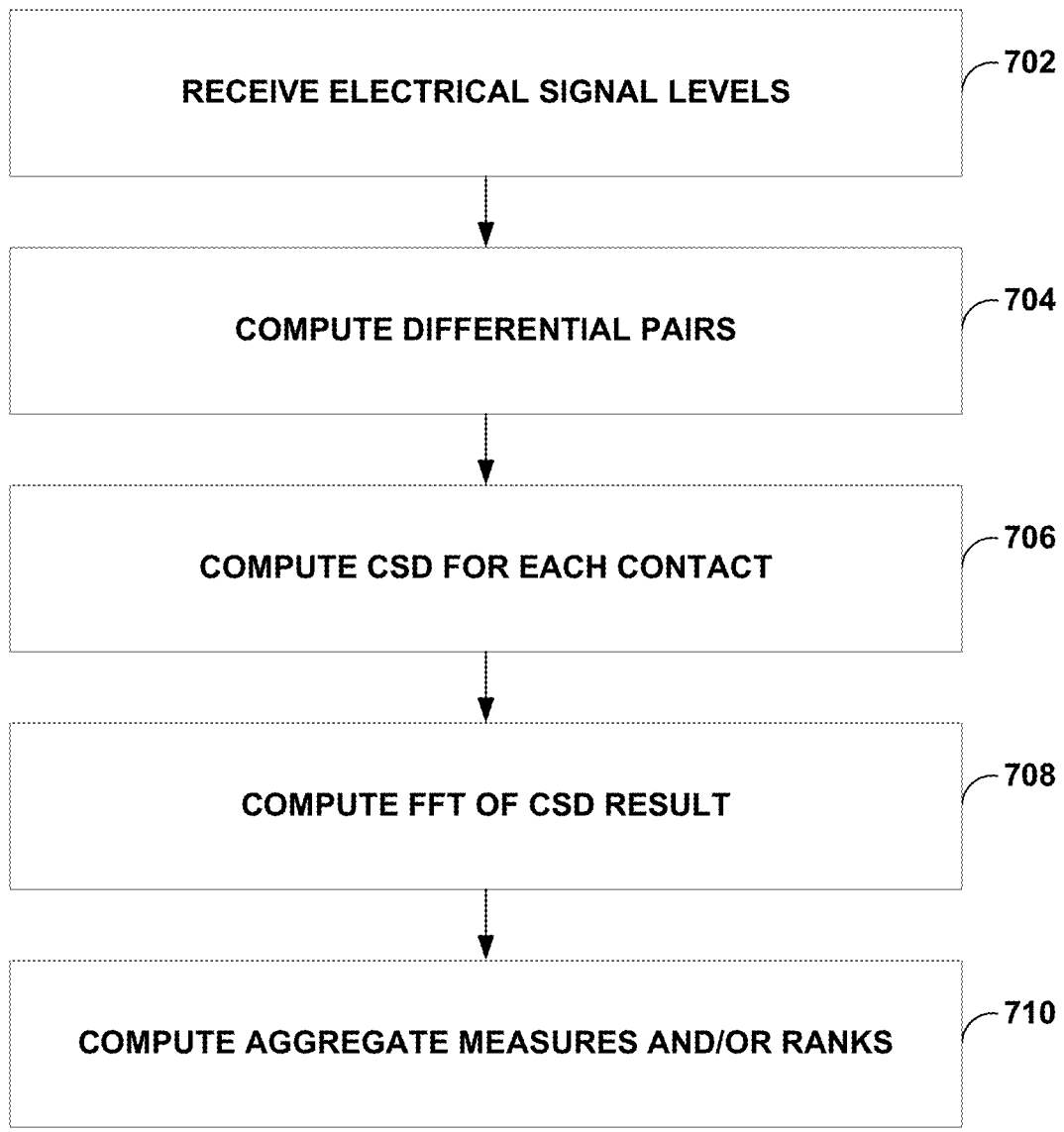
FIG. 7 is a flowchart illustrating another example operation in accordance with techniques of the disclosure.

FIG. 7 is a flowchart illustrating another example operation in accordance with techniques of the disclosure. In the example, processing circuitry 210 may receive electrical signal levels (e.g., voltage measurements) from electrodes 116, 118 (702). For example, memory 211 may store the electrical signal levels and processing circuitry 210 may receive the electrical signal levels from memory 211. Processing circuitry 210 may compute differential pairs based on the electrical signal levels (e.g., $\Delta V_{i,i-1} - \Delta V_{i+1,i}$ and $\Delta V_{j,j-1} - \Delta V_{j+1,j}$) (704). Processing circuitry 210 may compute CSD values for each contact (e.g., electrode) based on the computed differential pairs (e.g., determine $A_i(t)$ and $Z_i(t)$ and add them together to determine the CSD values) (706). Processing circuitry 210 may determine a fast Fourier transform (FFT) (or other types of transform from time-domain to frequency domain) of the CSD values (708). Processing circuitry 210 may compute aggregate measures and/or ranks (710). An example of the aggregate measurement is the average level value (e.g., RMS value), and an example of the rank is the phase-magnitude representation, as described above.

For example, the FFT results in a phasor in the frequency domain. These phasors $P_i$ can be subtracted across electrodes in a similar manner to the time domain approach described above (e.g., $P_{i,j-1} - P_{i+1,i}$ and $P_{j,j-1} - P_{j+1,j}$). If phase is dropped and |P| is used, then an approximation results. This may be most relevant if horizontal components are computed separately from vertical. Also, the RMS value is one example, and other techniques to determine the average level value includes sum(abs(CSD(t))), sum(squared(CSD(t)), sqrt(sum (squared(CSD(t)-mean(CSD(t))))), etc. The average level value may be determined using other techniques as well.

Figure 8:
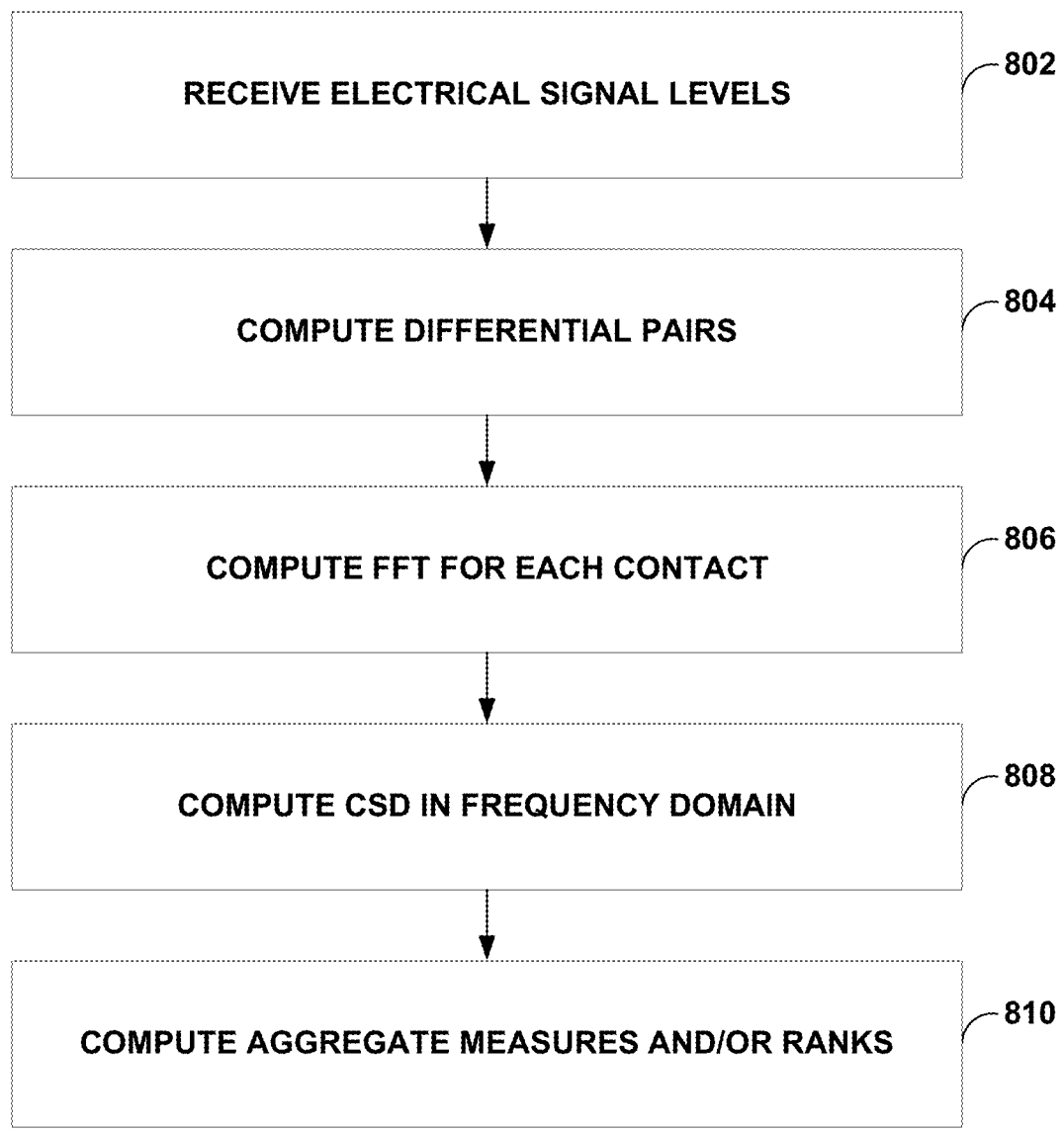
FIG. 8 is a flowchart illustrating another example operation in accordance with techniques of the disclosure.

FIG. 8 is a flowchart illustrating another example operation in accordance with techniques of the disclosure. In the example, processing circuitry 210 may receive electrical signal levels (e.g., voltage measurements) from electrodes 116, 118 (802). For example, memory 211 may store the electrical signal levels and processing circuitry 210 may receive the electrical signal levels from memory 211. Processing circuitry 210 may compute differential pairs based on the electrical signal levels (e.g., $\Delta V_{i,i-1} - \Delta V_{i+1,i}$ and $\Delta V_{j,j-1} - \Delta V_{j+1,j}$) (804). Processing circuitry 210 may determine a fast Fourier transform (FFT) (or other types of transform from time-domain to frequency domain) of the CSD values for each contact (806). Processing circuitry 210 may compute the CSD values in the frequency domain as described above (808). Processing circuitry 210 may compute aggregate measures and/or ranks (810). An example of the aggregate measurement is the average level value (e.g., RMS value), and an example of the rank is the phase-magnitude representation, as described above. Also, the RMS value is one example, and other techniques to determine the average level value includes sum(abs(CSD(t))), sum(squared(CSD(t)), sqrt(sum(squared(CSD(t)-mean (CSD(t))))), etc. The average level value may be determined using other techniques as well.

Figure 9:
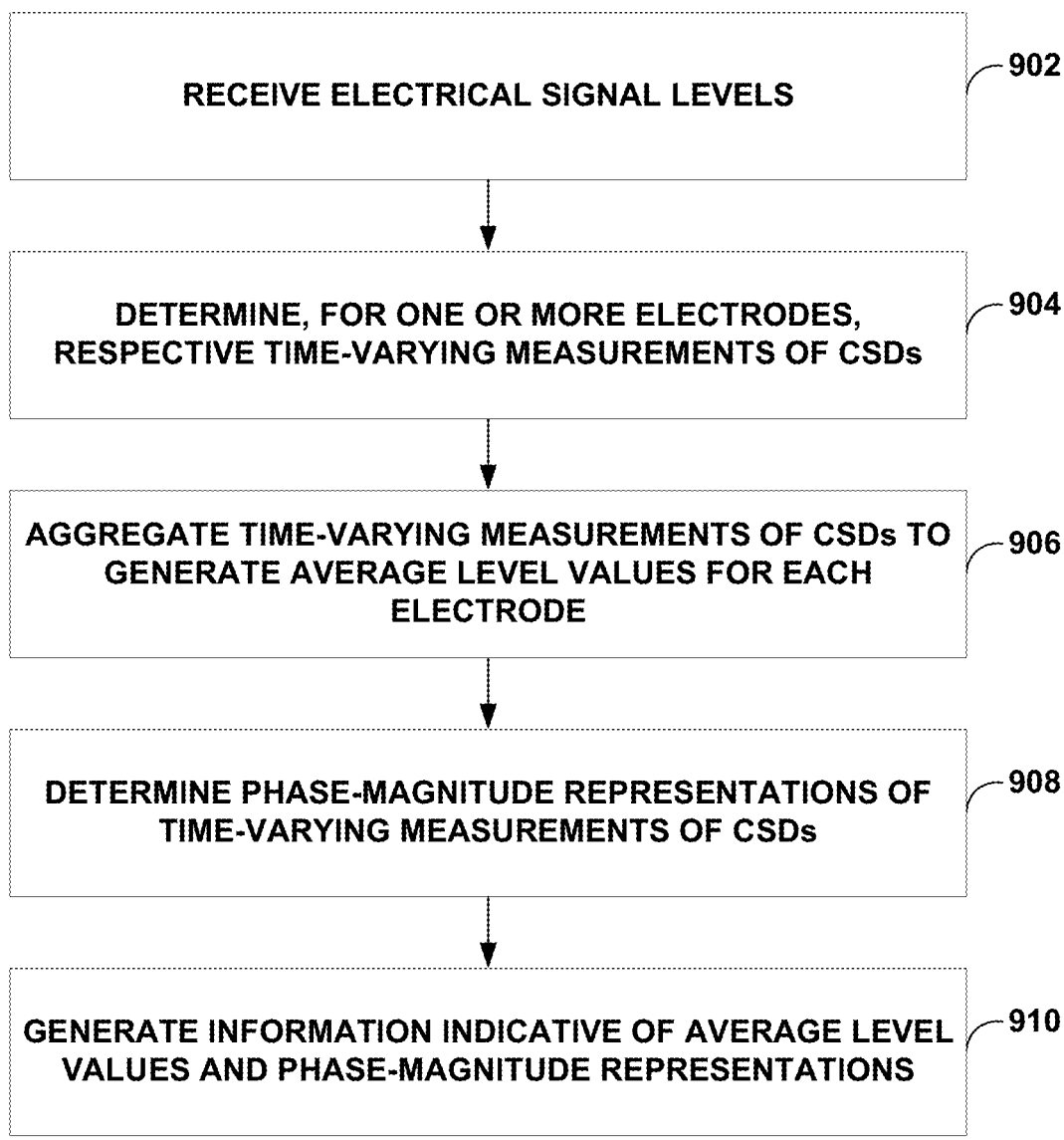
FIG. 9 is a flowchart illustrating another example operation in accordance with techniques of the disclosure.

FIG. 9 is a flowchart illustrating another example operation in accordance with techniques of the disclosure. For ease of description, the example is described with respect to processing circuitry 210 but the operations may be performed by processing circuitry 310 or a combination of processing circuitry 210 and processing circuitry 310.

Processing circuitry 210 may receive electrical signal levels (e.g., voltage measurements but other types of electrical signal levels are possible) from electrodes 116, 118 (902). For example, memory 211 may store the electrical signal levels and processing circuitry 210 may receive the electrical signal levels from memory 211. The voltages at electrodes 116, 118 may be the result of an oscillatory signal source sinking or sourcing current, which forms a voltage on electrodes 116, 118.

Processing circuitry 210 may determine, for one or more electrodes of the plurality of electrodes 116 and 118, respective time-varying measurements of CSDs (904). Processing circuitry 210 may perform the operations from any one or combination of (if applicable) the techniques described with respect to FIGS. 5-8.

As one example, processing circuitry 210 may determine, for one or more electrodes of the plurality of electrodes, respective first time-varying measurements based on second-order voltage differences between two electrodes that horizontally neighbor each electrode and a horizontal distance between the two horizontally neighboring electrodes and determine, for one or more electrodes of the plurality of electrodes, respective second time-varying measurements based on second-order voltage differences between two electrodes that vertically neighbor each electrode and a vertical distance between the two vertically neighboring electrodes. Processing circuitry 210 may determine respective time-varying measurements of the CSDs based on the respective first time-varying measurements and the second time-varying measurements.

As one example, processing circuitry 210 may scale the respective first-time varying measurements based on a radius of leads 114A, B that includes the respective electrodes of electrodes 116, 118 (e.g., determine $A_i(t)$ as described above by scaling by a factor of 1/r). Also, in some examples, processing circuitry 210 may scale at least one of the respective first time-varying measurements or the second time-varying measurements based on an anisotropy of local tissue impedance of the two horizontally neighboring electrodes or the two vertically neighboring electrodes. For instance, processing circuitry 210 may multiply the first and second time-varying measurements by of the CSDs by σ.

Processing circuitry 210 may be configured to aggregate, for one or more electrodes of the plurality of electrodes 116, 118, the respective time-varying measurements of the CSDs to generate respective average level values for one or more electrodes of the plurality of electrodes (906). For example, processing circuitry 210 may be configured to determine, for one or more electrodes of the plurality of electrodes 116, 118, respective root-mean-square (RMS) values based on the respective first time-varying measurement and the second time-varying measurement. As described above, processing circuitry 210 may perform the operations of the following equation to generate the average level value as a way to aggregate the respective time-varying measurements of the CSDs $$CSD_i^{RMS} = \sigma \sqrt{\frac{1}{N} \sum_{j=1}^{N} |A_i(j) + Z_i(j)|^2},$$

where i is the electrode of interest, and N is the number of data points in a temporal window of CSD values that are determined. Techniques other than techniques to calculate RMS values may be used to aggregate time-varying measurements of the CSD values.

In addition to generating the average level values, processing circuitry 210 may determine for one or more electrodes of the plurality of electrodes 116, 118, respective phase-magnitude representations of the time-varying measurements of the CSDs (908). The respective phase-magnitude representations are indicative of respective magnitudes and phases of a particular frequency component of respective time-varying measurements of the CSDs, where the particular frequency component is a frequency component having a largest transform coefficient in a time-varying measurement of a CSD having a largest average level value. There may be various ways in which to determine the phase-magnitude representation. One of the example ways in which to determine the phase-magnitude representation is described above and in more detail with respect to FIG. 10.

In some examples, processing circuitry 210 may be configured to generate information indicative of the respective average level values and respective phase-magnitude representations (910). As one example, processing circuitry 210 may output color information that represents the different average level values for the electrodes and output color information for the phase, where the opacity of the color for the phase is based on the magnitude. As another example, processing circuitry 210 may output average level values and phase-magnitude representations as data values.

In some examples, processing circuitry 210 may be configured to determine which electrodes of the one or more electrodes 116, 118 are most proximate, distal, or in between proximate and distal to an oscillatory signal source based on the generated information indicative of the respective average level values and the respective phase-magnitude representations. In such examples, processing circuitry 210 may generate and output information indicative of the determined electrodes.

The example techniques of FIG. 9 may be used for any one or combination of the following. The example techniques may be performed in a peripheral device (e.g. a patient or physician programmer 104) or cloud platform, and presented to the physician as an electrode selection, recommendation based on the largest/smallest value, or ranking of electrodes based on value and/or could be used to program IMD 106 to deliver stimulation with the electrode selection on a semi-automatic or automatic basis. The example techniques could be computed on IMD 106 and selected automatically. The example techniques could be computed on IMD 106 and presented on a peripheral device (e.g. a patient or physician programmer 104) or cloud platform, to the physician as a recommendation based on the largest/smallest value, or ranking of electrodes based on value.

Figure 10:
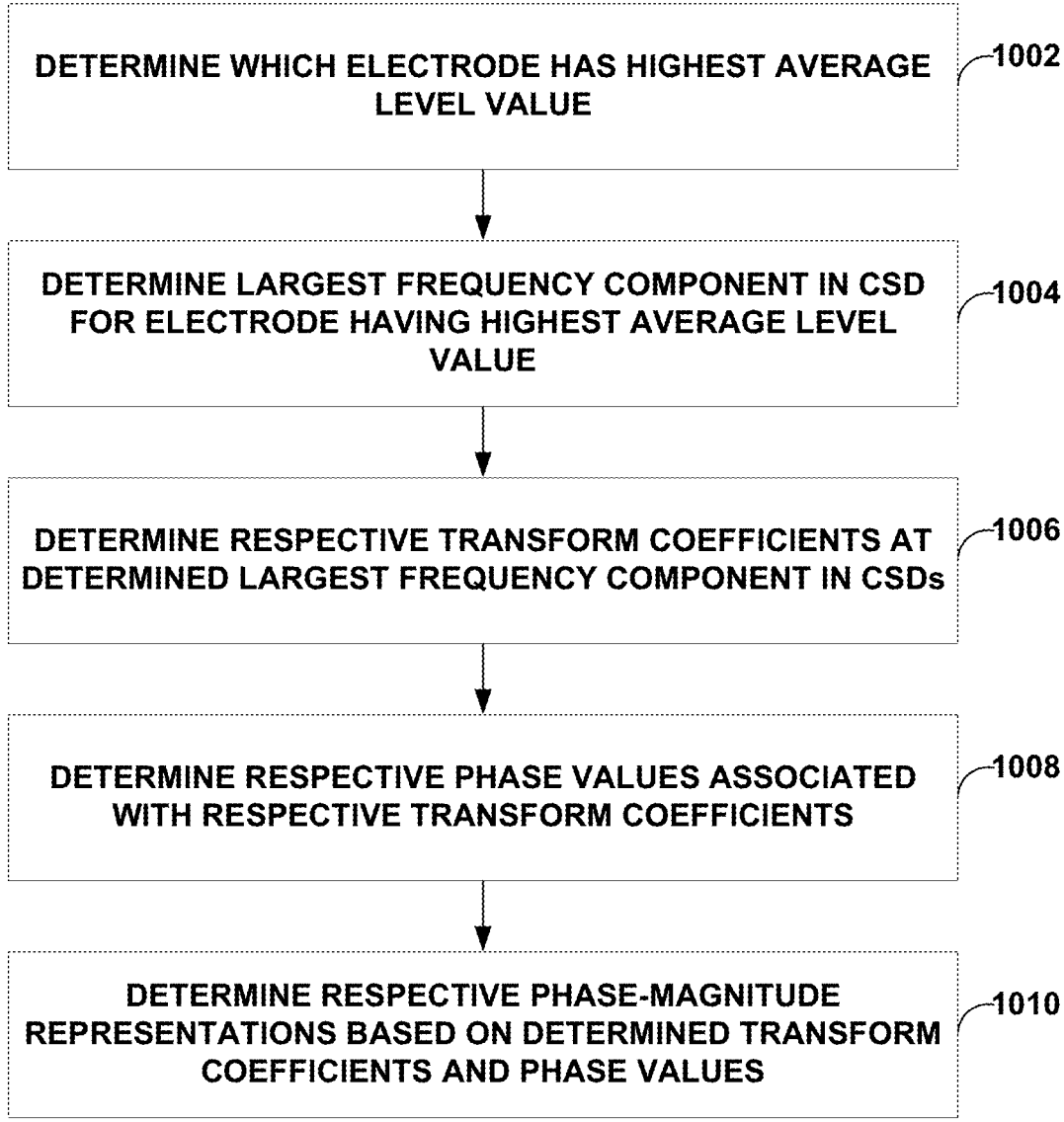
FIG. 10 is a flowchart illustrating another example operation in accordance with techniques of the disclosure.

FIG. 10 is a flowchart illustrating another example operation in accordance with techniques of the disclosure. For ease of description, the example is described with respect to processing circuitry 210 but the operations may be performed by processing circuitry 310 or a combination of processing circuitry 210 and processing circuitry 310.

Processing circuitry 210 may determine which electrode of electrodes 116, 118 has a highest average level value (1002) and determine a largest frequency component in the time-varying measurement of the CSD for the electrode having the highest average level value (1004). For example, assume that electrode X has the highest average level value of the time-varying measurements of the CSDs, and assume that frequency w0 is the largest frequency component in the time-varying measurement CSD at electrode X.

Processing circuitry 210 may determine, for one or more electrodes of the plurality of electrodes 116, 118, respective transform coefficients (e.g., Fourier transform coefficients (FTCs)) at the determined largest frequency component (e.g., w0) in respective time-varying measurements of the CSDs (1006). Processing circuitry 210 may also determine, for one or more electrodes of the plurality of electrodes 116, 118, respective phase values associated with the respective transform coefficients (1008). For example, assume that $A_{w0,i}$ is the FTC for frequency w0 for the ith electrode, and is equal to $M_i e^{j\phi_i}$. In this example, $M_i$ is the magnitude of frequency component with frequency w0, $\phi_i$ is the phase of the frequency component with frequency w0 (e.g., phase value associated with transform coefficient), and j is the square-root of −1.

Processing circuitry 210 may determining respective phase-magnitude representations based on the determined respective transform coefficients and the respective phase values (1010). For example, processing circuitry 210 may utilize the $M_i$ and $\phi_i$ values to determine respective phase-magnitude representations for electrode i. As one example, processing circuitry 210 may determine a largest transform coefficient from the respective transform coefficients. For instance, $A_{w0,k}$ represents the largest transform coefficient and is the coefficient of electrode-k. $A_{w0,k}$ equals $M_k e^{j\phi_k}$. Processing circuitry 210 may determine a phase value associated with the determined largest transform coefficient (e.g., determine $\phi_k$). Processing circuitry 210 determine a difference between respective phase values associated with respective transform coefficients and the determined phase value associated with the determined largest transform coefficient (e.g., determine ($\phi_i - \phi_k$)). Processing circuitry 210 may determine respective phase-magnitude representations based on the determined difference and the determined respective transform coefficients (e.g., $A_{w0,i\_norm}$ equals $M_i e^{j(\phi_i - \phi_k)}$).

In some examples, the above example operations described with FIGS. 5-10 and elsewhere may be performed multiple times across multiple sub-bands (e.g., different frequency band) to detect locations of multiple sources that might appear as one big source. For instance, the above example techniques are described as being performed over the beta band, but in some examples, IMD 106 and/or programmer 104 may perform the example operations at different bands to identify multiple oscillatory sources.

Figure 11:
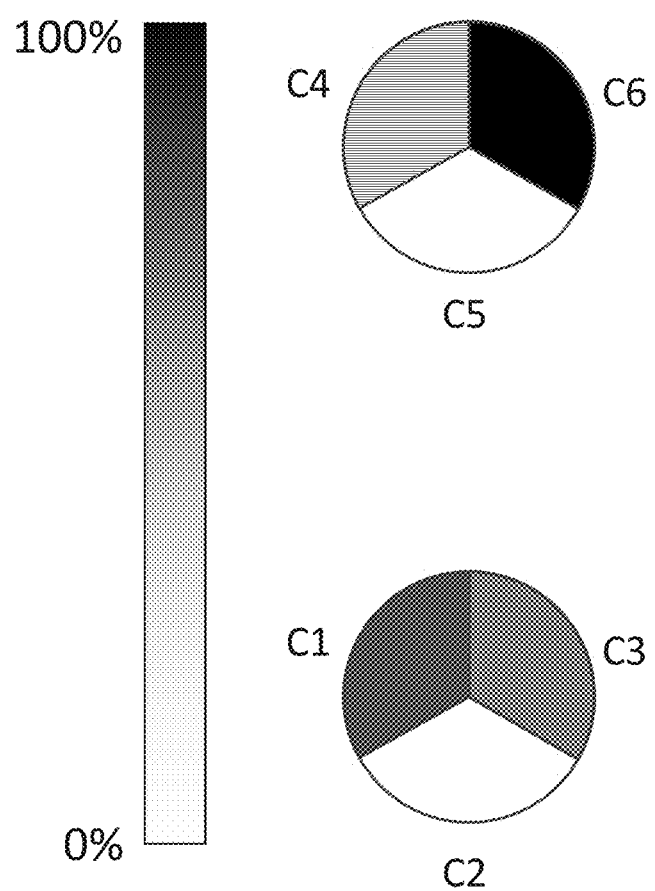
FIG. 11 is a conceptual diagram illustrating example of average CSD values for a plurality of electrodes.

FIG. 11 is a conceptual diagram illustrating example of average CSD values for a plurality of electrodes. FIG. 11 illustrates the average CSD values (e.g., average level values) for electrodes C1-C6, where electrodes C1-C3 are at the same level and electrodes C4-C6 are at the same level. In FIG. 11, the average level values for the time-varying signals from electrodes C4 and C6 may be greatest, the average level values for the time-varying signals from electrodes C1 and C3 may be between the greatest and smallest, with the average level value for electrode C1 being greater than that for electrode C3, and the average level values for the time-varying signals for electrodes C2 and C5 may be the smallest.

FIG. 12 is a conceptual diagram illustrating example phase-magnitude representation for CSDs for a plurality of electrodes. FIG. 12 illustrates the phase-magnitude representation (e.g., normalized phase-magnitude representation, but such normalization may not be necessary in all examples) for electrodes C1-C6, where electrodes C1-C3 are at the same level and electrodes C4-C6 are at the same level. In the example of FIG. 12, the time-varying signal from electrode C3 may provide the reference phase (e.g., $\phi_k$ is phase of the time-varying signal at electrode C3 for the frequency component w0, where frequency component w0 is a frequency component having a largest transform coefficient in a time-varying measurement of a CSD having a largest average level value).

The gray-scale level of electrodes C1-C6 may be based on the value of $A_{w0,i\_norm}$ (e.g., the greater the value of $A_{w0,i\_norm}$, the darker the electrode is shown in FIG. 12). Also, the arrows shown within electrodes C1-C6 are indicative of an amount of phase difference from reference phase (e.g., $(\phi_i - \phi_k)$). For example, for electrodes C4 and C5, the arrows indicate that their respective values of $(\phi_i - \phi_k)$ is close to 0-degrees or 360-degrees (e.g., 0 or $2\pi$). For electrodes C1 and C2, the arrows indicate that their respective values of $(\phi_i - \phi_k)$ is close to 180-degrees (e.g., $\pi$). Accordingly, in this example, the phase difference between electrodes C4 and C5 and electrodes C1 and C2 is approximately 180-degrees. Therefore, electrodes C4 and C5 may be proximate to tissue that is acting like a signal source or signal sink, and electrodes C1 and C2 may be proximate to tissue that is acting as the signal sink, if tissue proximate to electrodes C4 and C5 is acting like a signal source, or acting as a signal source, if tissue proximate to electrodes C4 and C5 is acting like a signal sink. In this example, electrodes C3 and C6 may be distal to tissue acting like signal source or signal sink.

The following examples are example systems, devices, and methods described herein.

Example 1. A method comprising determining, for one or more electrodes of a plurality of electrodes, respective time-varying measurements of current source densities (CSDs), aggregating, for the one or more electrodes of the plurality electrodes, the respective time-varying measurements of the CSDs to generate respective average level values for the one or more electrodes of the plurality of electrodes, determining, for one or more electrodes of the plurality of electrodes, respective phase-magnitude representations of the time-varying measurements of the CSDs, wherein the respective phase-magnitude representations are indicative of respective magnitudes and phases of a particular frequency component of respective time-varying measurements of the CSDs and wherein the particular frequency component is a frequency component having a largest transform coefficient in a time-varying measurement of a CSD having a largest average level value, and generating information indicative of the respective average level values and respective phase-magnitude representations.

Example 2. The method of example 1, further comprising determining which electrodes of the one or more electrodes are most proximate or distal to an oscillatory signal source based on the generated information of the respective average level values and the respective phase-magnitude representations and generating information indicative of the determined electrodes.

Example 3. The method of any of examples 1 and 2, wherein determining respective time-varying measurements of the CSDs comprises determining, for one or more electrodes of the plurality of electrodes, respective first time-varying measurements based on second-order voltage differences between two electrodes that horizontally neighbor each respective electrode and a horizontal distance between the two horizontally neighboring electrodes, determining, for one or more electrodes of the plurality of electrodes, respective second time-varying measurements based on second-order voltage differences between two electrodes that vertically neighbor each respective electrode and a vertical distance between the two vertically neighboring electrodes, and determining the respective time-varying measurements of the CSDs based on the respective first time-varying measurements and the second time-varying measurements.

Example 4. The method of example 3, further comprising scaling the respective first time-varying measurements based on a radius of an implantable lead that includes the respective electrodes, wherein determining respective time-varying measurements of the CSDs comprises determining respective time-varying measurements of the CSDs based on the respective scaled first time-varying measurements and the second time-varying measurements.

Example 5. The method of any of examples 3 and 4, further comprising scaling at least one of the respective first time-varying measurements or the second time-varying measurements based on an anisotropy of local tissue impedance of the two horizontally neighboring electrodes or the two vertically neighboring electrodes, wherein determining respective time-varying measurements of the CSDs comprises determining respective time-varying measurements of the CSDs based on the respective scaled first time-varying measurements or the respective scaled second time-varying measurements.

Example 6. The method of any of examples 1-5, wherein determining respective phase-magnitude representations comprises determining which of the one or more electrodes has a highest average level value, determining a largest frequency component in the time-varying measurement of the CSD for the electrode having the highest average level value, determining, for one or more electrodes of the plurality of electrodes, respective transform coefficients at the determined largest frequency component in respective time-varying measurements of the CSDs, determining, for one or more electrodes of the plurality of electrodes, respective phase values associated with the respective transform coefficients, and determining the respective phase-magnitude representations based on the determined respective transform coefficients and the respective phase values.

Example 7. The method of example 6, wherein determining respective phase-magnitude representations based on the determined respective transform coefficients and the respective phase values comprises determining a largest transform coefficient from the respective transform coefficients, determining a phase value associated with the determined largest transform coefficient, determining differences between respective phase values associated with respective transform coefficients and the determined phase value associated with the determined largest transform coefficient, and determining respective phase-magnitude representations based on the determined differences and the determined respective transform coefficients.

Example 8. A system comprising a memory configured to store electrical signal levels and processing circuitry configured to determine, for one or more electrodes of a plurality of electrodes, respective time-varying measurements of current source densities (CSDs) based on the electrical signal levels, aggregate, for the one or more electrodes of the plurality electrodes, the respective time-varying measurements of the CSDs to generate respective average level values for the one or more electrodes of the plurality of electrodes, determine, for one or more electrodes of the plurality of electrodes, respective phase-magnitude representations of the time-varying measurements of the CSDs, wherein the respective phase-magnitude representations are indicative of respective magnitudes and phases of a particular frequency component of respective time-varying measurements of the CSDs, wherein the particular frequency component is a frequency component having a largest transform coefficient in a time-varying measurement of a CSD having a largest average level value, and generate information indicative of the respective average level values and respective phase-magnitude representations.

Example 9. The system of example 8, further comprising an implantable medical device (IMD), wherein the IMD comprises the processing circuitry.

Example 10. The system of any of examples 8 and 9, further comprising a programmer comprising a display configured to display the information indicative of the respective average level values and respective phase-magnitude representations.

Example 11. The system of any of examples 8-10, wherein the processing circuitry is configured to determine which electrodes of the one or more electrodes are most proximate or distal to an oscillatory signal source based on the generated information of the respective average level values and the respective phase-magnitude representations and generate information indicative of the determined electrodes.

Example 12. The system of any of examples 8-11, wherein to determine respective time-varying measurements of the CSDs, the processing circuitry is configured to determine, for one or more electrodes of the plurality of electrodes, respective first time-varying measurements based on second-order voltage differences between two electrodes that horizontally neighbor each respective electrode and a horizontal distance between the two horizontally neighboring electrodes, determine, for one or more electrodes of the plurality of electrodes, respective second time-varying measurements based on second-order voltage differences between two electrodes that vertically neighbor each respective electrode and a vertical distance between the two vertically neighboring electrodes, and determine the respective time-varying measurements of the CSDs based on the respective first time-varying measurements and the second time-varying measurements.

Example 13. The system of example 12, wherein the processing circuitry is configured to scale the respective first time-varying measurements based on a radius of an implantable lead that includes the respective electrodes, wherein to determine respective time-varying measurements of the CSDs, the processing circuitry is configured to determine respective time-varying measurements of the CSDs based on the respective scaled first time-varying measurements and the second time-varying measurements.

Example 14. The system of any of examples 12 and 13, wherein the processing circuitry is configured to scale at least one of the respective first time-varying measurements or the second time-varying measurements based on an anisotropy of local tissue impedance of the two horizontally neighboring electrodes or the two vertically neighboring electrodes, wherein to determine respective time-varying measurements of the CSDs, the processing circuitry is configured to determine respective time-varying measurements of the CSDs based on the respective scaled first time-varying measurements or the respective scaled second time-varying measurements.

Example 15. The system of any of examples 8-14, wherein to determine respective phase-magnitude representations, the processing circuitry is configured to determine which of the one or more electrodes has a highest average level value, determine a largest frequency component in the time-varying measurement of the CSD for the electrode having the highest average level value, determine, for one or more electrodes of the plurality of electrodes, respective transform coefficients at the determined largest frequency component in respective time-varying measurements of the CSDs, determine, for one or more electrodes of the plurality of electrodes, respective phase values associated with the respective transform coefficients, and determine the respective phase-magnitude representations based on the determined respective transform coefficients and the respective phase values.

Example 16. The system of example 15, wherein to determine respective phase-magnitude representations based on the determined respective transform coefficients and the respective phase values, the processing circuitry is configured to determine a largest transform coefficient from the respective transform coefficients, determine a phase value associated with the determined largest transform coefficient, determine differences between respective phase values associated with respective transform coefficients and the determined phase value associated with the determined largest transform coefficient, and determine respective phase-magnitude representations based on the determined differences and the determined respective transform coefficients.

Example 17. A computer-readable storage medium comprising instructions that when executed cause one or more processors to determine, for one or more electrodes of a plurality of electrodes, respective time-varying measurements of current source densities (CSDs), aggregate, for the one or more electrodes of the plurality electrodes, the respective time-varying measurements of the CSDs to generate respective average level values for the one or more electrodes of the plurality of electrodes, determine, for one or more electrodes of the plurality of electrodes, respective phase-magnitude representations of the time-varying measurements of the CSDs, wherein the respective phase-magnitude representations are indicative of respective magnitudes and phases of a particular frequency component of respective time-varying measurements of the CSDs, wherein the particular frequency component is a frequency component having a largest transform coefficient in a time-varying measurement of a CSD having a largest average level value, and generate information indicative of the respective average level values and respective phase-magnitude representations.

Example 18. The computer-readable storage medium of example 17, further comprising instructions that cause the one or more processors to determine which electrodes of the one or more electrodes are most proximate or distal to an oscillatory signal source based on the generated information of the respective average level values and the respective phase-magnitude representations and generate information indicative of the determined electrodes.

Example 19. The computer-readable storage medium of any of examples 17 and 18, wherein the instructions that cause the one or more processors to determine respective time-varying measurements of the CSDs comprise instructions that cause the one or more processors to determine, for one or more electrodes of the plurality of electrodes, respective first time-varying measurements based on second-order voltage differences between two electrodes that horizontally neighbor each respective electrode and a horizontal distance between the two horizontally neighboring electrodes, determine, for one or more electrodes of the plurality of electrodes, respective second time-varying measurements based on second-order voltage differences between two electrodes that vertically neighbor each respective electrode and a vertical distance between the two vertically neighboring electrodes, and determine the respective time-varying measurements of the CSDs based on the respective first time-varying measurements and the second time-varying measurements.

Example 20. The computer-readable storage medium of example 19, further comprising instructions that cause the one or more processors to scale the respective first time-varying measurements based on a radius of an implantable lead that includes the respective electrodes, wherein the instructions that cause the one or more processors to determine respective time-varying measurements of the CSDs comprise instructions that cause the one or more processors to determine respective time-varying measurements of the CSDs based on the respective scaled first time-varying measurements and the second time-varying measurements.

Example 21. The computer-readable storage medium of any of examples 19 and 20, further comprising instructions that cause the one or more processors to scale at least one of the respective first time-varying measurements or the second time-varying measurements based on an anisotropy of local tissue impedance of the two horizontally neighboring electrodes or the two vertically neighboring electrodes, wherein the instructions that cause the one or more processors to determine respective time-varying measurements of the CSDs comprise instructions that cause the one or more processors to determine respective time-varying measurements of the CSDs based on the respective scaled first time-varying measurements or the respective scaled second time-varying measurements.

Example 22. The computer-readable storage medium of any of examples 17-21, wherein the instructions that cause the one or more processors to determine respective phase-magnitude representations comprise instructions that cause the one or more processors to determine which of the one or more electrodes has a highest average level value, determine a largest frequency component in the time-varying measurement of the CSD for the electrode having the highest average level value, determine, for one or more electrodes of the plurality of electrodes, respective transform coefficients at the determined largest frequency component in respective time-varying measurements of the CSDs, determine, for one or more electrodes of the plurality of electrodes, respective phase values associated with the respective transform coefficients, and determine the respective phase-magnitude representations based on the determined respective transform coefficients and the respective phase values.

Example 23. The computer-readable storage medium of example 22, wherein the instructions that cause the one or more processors to determine respective phase-magnitude representations based on the determined respective transform coefficients and the respective phase values comprise instructions that cause the one or more processors to determine a largest transform coefficient from the respective transform coefficients, determine a phase value associated with the determined largest transform coefficient, determine differences between respective phase values associated with respective transform coefficients and the determined phase value associated with the determined largest transform coefficient, and determine respective phase-magnitude representations based on the determined differences and the determined respective transform coefficients.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. A method comprising:
   determining, for one or more electrodes of a plurality of electrodes, respective time-varying measurements of current source densities (CSDs);
   aggregating, for the one or more electrodes of the plurality electrodes, the respective time-varying measurements of the CSDs to generate respective average level values for the one or more electrodes of the plurality of electrodes;
   determining, for one or more electrodes of the plurality of electrodes, respective phase-magnitude representations of the time-varying measurements of the CSDs, wherein the respective phase-magnitude representations are indicative of respective magnitudes and phases of a particular frequency component of respective time-varying measurements of the CSDs and wherein the particular frequency component is a frequency component having a largest transform coefficient in a time-varying measurement of a CSD having a largest average level value; and
   generating information indicative of the respective average level values and respective phase-magnitude representations.

2. The method of claim 1, further comprising:
   determining which electrodes of the one or more electrodes are most proximate or distal to an oscillatory signal source based on the generated information of the respective average level values and the respective phase-magnitude representations; and
   generating information indicative of the determined electrodes.

3. The method of claim 1, wherein determining respective time-varying measurements of the CSDs comprises:
   determining, for one or more electrodes of the plurality of electrodes, respective first time-varying measurements based on second-order voltage differences between two electrodes that horizontally neighbor each respective electrode and a horizontal distance between the two horizontally neighboring electrodes;
   determining, for one or more electrodes of the plurality of electrodes, respective second time-varying measurements based on second-order voltage differences between two electrodes that vertically neighbor each respective electrode and a vertical distance between the two vertically neighboring electrodes; and
   determining the respective time-varying measurements of the CSDs based on the respective first time-varying measurements and the second time-varying measurements.

4. The method of claim 3, further comprising:
   scaling the respective first time-varying measurements based on a radius of an implantable lead that includes the respective electrodes,
   wherein determining respective time-varying measurements of the CSDs comprises determining respective time-varying measurements of the CSDs based on the respective scaled first time-varying measurements and the second time-varying measurements.

5. The method of claim 3, further comprising:
   scaling at least one of the respective first time-varying measurements or the second time-varying measurements based on an anisotropy of local tissue impedance of the two horizontally neighboring electrodes or the two vertically neighboring electrodes,
   wherein determining respective time-varying measurements of the CSDs comprises determining respective time-varying measurements of the CSDs based on the respective scaled first time-varying measurements or the respective scaled second time-varying measurements.

6. The method of claim 1, wherein determining respective phase-magnitude representations comprises:
   determining which of the one or more electrodes has a highest average level value;
   determining a largest frequency component in the time-varying measurement of the CSD for the electrode having the highest average level value;
   determining, for one or more electrodes of the plurality of electrodes, respective transform coefficients at the determined largest frequency component in respective time-varying measurements of the CSDs;
   determining, for one or more electrodes of the plurality of electrodes, respective phase values associated with the respective transform coefficients; and
   determining the respective phase-magnitude representations based on the determined respective transform coefficients and the respective phase values.

7. The method of claim 6, wherein determining respective phase-magnitude representations based on the determined respective transform coefficients and the respective phase values comprises:
   determining a largest transform coefficient from the respective transform coefficients;
   determining a phase value associated with the determined largest transform coefficient;
   determining differences between respective phase values associated with respective transform coefficients and the determined phase value associated with the determined largest transform coefficient; and
   determining respective phase-magnitude representations based on the determined differences and the determined respective transform coefficients.

8. A system comprising:
   a memory configured to store electrical signal levels; and
   processing circuitry configured to:
      determine, for one or more electrodes of a plurality of electrodes, respective time-varying measurements of current source densities (CSDs) based on the electrical signal levels;
      aggregate, for the one or more electrodes of the plurality electrodes, the respective time-varying measurements of the CSDs to generate respective average level values for the one or more electrodes of the plurality of electrodes;
      determine, for one or more electrodes of the plurality of electrodes, respective phase-magnitude representations of the time-varying measurements of the CSDs, wherein the respective phase-magnitude representations are indicative of respective magnitudes and phases of a particular frequency component of respective time-varying measurements of the CSDs, wherein the particular frequency component is a frequency component having a largest transform coefficient in a time-varying measurement of a CSD having a largest average level value; and
      generate information indicative of the respective average level values and respective phase-magnitude representations.

9. The system of claim 8, further comprising an implantable medical device (IMD), wherein the IMD comprises the processing circuitry.

10. The system of claim 8, further comprising a programmer comprising a display configured to display the information indicative of the respective average level values and respective phase-magnitude representations.

11. The system of claim 8, wherein the processing circuitry is configured to:
   determine which electrodes of the one or more electrodes are most proximate or distal to an oscillatory signal source based on the generated information of the respective average level values and the respective phase-magnitude representations; and
   generate information indicative of the determined electrodes.

12. The system of claim 8, wherein to determine respective time-varying measurements of the CSDs, the processing circuitry is configured to:
   determine, for one or more electrodes of the plurality of electrodes, respective first time-varying measurements based on second-order voltage differences between two electrodes that horizontally neighbor each respective electrode and a horizontal distance between the two horizontally neighboring electrodes;
   determine, for one or more electrodes of the plurality of electrodes, respective second time-varying measurements based on second-order voltage differences between two electrodes that vertically neighbor each respective electrode and a vertical distance between the two vertically neighboring electrodes; and
   determine the respective time-varying measurements of the CSDs based on the respective first time-varying measurements and the second time-varying measurements.

13. The system of claim 12, wherein the processing circuitry is configured to:
   scale the respective first time-varying measurements based on a radius of an implantable lead that includes the respective electrodes,
   wherein to determine respective time-varying measurements of the CSDs, the processing circuitry is configured to determine respective time-varying measurements of the CSDs based on the respective scaled first time-varying measurements and the second time-varying measurements.

14. The system of claim 12, wherein the processing circuitry is configured to:
   scale at least one of the respective first time-varying measurements or the second time-varying measurements based on an anisotropy of local tissue impedance of the two horizontally neighboring electrodes or the two vertically neighboring electrodes,
   wherein to determine respective time-varying measurements of the CSDs, the processing circuitry is configured to determine respective time-varying measurements of the CSDs based on the respective scaled first time-varying measurements or the respective scaled second time-varying measurements.

15. The system of claim 8, wherein to determine respective phase-magnitude representations, the processing circuitry is configured to:
   determine which of the one or more electrodes has a highest average level value;
   determine a largest frequency component in the time-varying measurement of the CSD for the electrode having the highest average level value;
   determine, for one or more electrodes of the plurality of electrodes, respective transform coefficients at the determined largest frequency component in respective time-varying measurements of the CSDs;
   determine, for one or more electrodes of the plurality of electrodes, respective phase values associated with the respective transform coefficients; and
   determine the respective phase-magnitude representations based on the determined respective transform coefficients and the respective phase values.

16. The system of claim 15, wherein to determine respective phase-magnitude representations based on the determined respective transform coefficients and the respective phase values, the processing circuitry is configured to:
   determine a largest transform coefficient from the respective transform coefficients;
   determine a phase value associated with the determined largest transform coefficient;
   determine differences between respective phase values associated with respective transform coefficients and the determined phase value associated with the determined largest transform coefficient; and
   determine respective phase-magnitude representations based on the determined differences and the determined respective transform coefficients.

17. A computer-readable storage medium comprising instructions that when executed cause one or more processors to:
   determine, for one or more electrodes of a plurality of electrodes, respective time-varying measurements of current source densities (CSDs);
   aggregate, for the one or more electrodes of the plurality electrodes, the respective time-varying measurements of the CSDs to generate respective average level values for the one or more electrodes of the plurality of electrodes;
   determine, for one or more electrodes of the plurality of electrodes, respective phase-magnitude representations of the time-varying measurements of the CSDs, wherein the respective phase-magnitude representations are indicative of respective magnitudes and phases of a particular frequency component of respective time-varying measurements of the CSDs, wherein the particular frequency component is a frequency component having a largest transform coefficient in a time-varying measurement of a CSD having a largest average level value; and
   generate information indicative of the respective average level values and respective phase-magnitude representations.

18. The computer-readable storage medium of claim 17, further comprising instructions that cause the one or more processors to:
   determine which electrodes of the one or more electrodes are most proximate or distal to an oscillatory signal source based on the generated information of the respective average level values and the respective phase-magnitude representations; and
   generate information indicative of the determined electrodes.

19. The computer-readable storage medium of claim 17, wherein the instructions that cause the one or more processors to determine respective time-varying measurements of the CSDs comprise instructions that cause the one or more processors to:
   determine, for one or more electrodes of the plurality of electrodes, respective first time-varying measurements based on second-order voltage differences between two electrodes that horizontally neighbor each respective electrode and a horizontal distance between the two horizontally neighboring electrodes;

determine, for one or more electrodes of the plurality of electrodes, respective second time-varying measurements based on second-order voltage differences between two electrodes that vertically neighbor each respective electrode and a vertical distance between the two vertically neighboring electrodes; and determine the respective time-varying measurements of the CSDs based on the respective first time-varying measurements and the second time-varying measurements.

20. The computer-readable storage medium of claim 19, further comprising instructions that cause the one or more processors to:

scale the respective first time-varying measurements based on a radius of an implantable lead that includes the respective electrodes, wherein the instructions that cause the one or more processors to determine respective time-varying measurements of the CSDs comprise instructions that cause the one or more processors to determine respective time-varying measurements of the CSDs based on the respective scaled first time-varying measurements and the second time-varying measurements.

21. The computer-readable storage medium of claim 19, further comprising instructions that cause the one or more processors to:

scale at least one of the respective first time-varying measurements or the second time-varying measurements based on an anisotropy of local tissue impedance of the two horizontally neighboring electrodes or the two vertically neighboring electrodes, wherein the instructions that cause the one or more processors to determine respective time-varying measurements of the CSDs comprise instructions that cause the one or more processors to determine respective time-varying measurements of the CSDs based on the respective scaled first time-varying measurements or the respective scaled second time-varying measurements.

22. The computer-readable storage medium of claim 17, wherein the instructions that cause the one or more processors to determine respective phase-magnitude representations comprise instructions that cause the one or more processors to:

determine which of the one or more electrodes has a highest average level value;

determine a largest frequency component in the time-varying measurement of the CSD for the electrode having the highest average level value;

determine, for one or more electrodes of the plurality of electrodes, respective transform coefficients at the determined largest frequency component in respective time-varying measurements of the CSDs;

determine, for one or more electrodes of the plurality of electrodes, respective phase values associated with the respective transform coefficients; and determine the respective phase-magnitude representations based on the determined respective transform coefficients and the respective phase values.

23. The computer-readable storage medium of claim 22, wherein the instructions that cause the one or more processors to determine respective phase-magnitude representations based on the determined respective transform coefficients and the respective phase values comprise instructions that cause the one or more processors to:

determine a largest transform coefficient from the respective transform coefficients;

determine a phase value associated with the determined largest transform coefficient;

determine differences between respective phase values associated with respective transform coefficients and the determined phase value associated with the determined largest transform coefficient; and determine respective phase-magnitude representations based on the determined differences and the determined respective transform coefficients.

* * * * *